(12) United States Patent
Jaillon et al.

(10) Patent No.: US 9,835,436 B2
(45) Date of Patent: Dec. 5, 2017

(54) WAVELENGTH ENCODED MULTI-BEAM OPTICAL COHERENCE TOMOGRAPHY

(71) Applicant: TOMEY CORPORATION, Nagoya-shi, Aichi (JP)

(72) Inventors: Franck E. M. Jaillon, Nagoya (JP); Naoko Hara, Nagoya (JP); Tsutomu Ohmori, Nagoya (JP); Chihiro Kato, Nagoya (JP)

(73) Assignee: Tomey Corporation, Nagoya (JP)

( * ) Notice: Subject to any disclaimer, the term of this patent is extended or adjusted under 35 U.S.C. 154(b) by 22 days.

(21) Appl. No.: 15/019,973

(22) Filed: Feb. 10, 2016

(65) Prior Publication Data
US 2016/0161244 A1    Jun. 9, 2016

Related U.S. Application Data

(63) Continuation-in-part of application No. 14/925,993, filed on Oct. 29, 2015, which is a continuation of
(Continued)

(51) Int. Cl.
*G01B 9/02* (2006.01)
*A61B 3/10* (2006.01)
(Continued)

(52) U.S. Cl.
CPC .......... *G01B 9/02091* (2013.01); *A61B 3/102* (2013.01); *G01B 9/02019* (2013.01);
(Continued)

(58) Field of Classification Search
CPC ............ G01B 9/02091; G01B 9/02027; G01B 9/02019
(Continued)

(56) References Cited

U.S. PATENT DOCUMENTS

| 5,900,928 A | 5/1999 | Riva et al. |
| 6,445,939 B1 | 9/2002 | Swanson et al. |

(Continued)

FOREIGN PATENT DOCUMENTS

| EP | 2719324 | 4/2014 |
| JP | 2011212204 | 10/2011 |

(Continued)

OTHER PUBLICATIONS

An et al., Optical microangiography provides correlation between microstructure and microvasculature of optic nerve head in human subjects, Journal of Biomedical Optics, vol. 17, No. 11 (Nov. 2012), pp. 116018-1, 116018-6.

(Continued)

*Primary Examiner* — Jonathan Hansen
(74) *Attorney, Agent, or Firm* — Patrick E. Caldwell, Esq.; The Caldwell Firm, LLC

(57) ABSTRACT

Optical coherence tomography (OCT) apparatuses and methods include a first electro-magnetic radiation (EMR) source providing EMR to a first optical path associated with a sample and a second optical path associated with a reference. A multi-beam generator unit (MBGU) generates first and second EMR beams having different wavelength contents. A scanning system illuminates the sample with the first and second EMR beams, at a first and second time, at a first and second location. An interference module generates interference signals based on received EMR returning from the reference and the first and second EMR beams returning from the sample. A detector generates detection signals based on received interference signals and a processor generates OCT data based on the processed detection signals. In some embodiments, three EMR beams having different wavelength contents with linearly independent vectors illuminate at least one same location of the sample.

20 Claims, 13 Drawing Sheets

FIG. 1a

Related U.S. Application Data application No. 14/069,626, filed on Nov. 1, 2013, now Pat. No. 9,200,888.

(51) Int. Cl.
 *G02B 5/09* (2006.01)
 *G02B 5/10* (2006.01)

(52) U.S. Cl.
 CPC ..... *G01B 9/02027* (2013.01); *G01B 9/02045* (2013.01); *G02B 5/09* (2013.01); *G02B 5/10* (2013.01)

(58) Field of Classification Search
 USPC .................................................. 356/479, 497
 See application file for complete search history.

(56) References Cited

U.S. PATENT DOCUMENTS

| | | | |
|---|---|---|---|
| 6,549,801 | B1 | 4/2003 | Chen et al. |
| 6,741,359 | B2 | 5/2004 | Wei et al. |
| 7,551,293 | B2 * | 6/2009 | Yelin ................ G01B 9/02027 356/456 |
| 2003/0020920 | A1 | 1/2003 | Dave et al. |
| 2003/0137669 | A1 | 7/2003 | Rollins et al. |
| 2009/0264707 | A1 | 10/2009 | Hendriks et al. |
| 2011/0242487 | A1 | 10/2011 | Yuasa et al. |
| 2012/0120408 | A1 | 5/2012 | Yasuno et al. |
| 2012/0176613 | A1 | 7/2012 | Marple et al. |
| 2012/0262722 | A1 | 10/2012 | Lim et al. |
| 2013/0003017 | A1 | 1/2013 | Muto |
| 2013/0321822 | A1 | 12/2013 | Vogler et al. |
| 2014/0016136 | A1 | 1/2014 | Kawano et al. |
| 2014/0078510 | A1 | 3/2014 | Rubio Guivernau et al. |
| 2014/0160488 | A1 * | 6/2014 | Zhou ................ G01B 9/02004 356/479 |
| 2015/0176969 | A1 | 6/2015 | Jensen |
| 2015/0176970 | A1 | 6/2015 | Jensen |

FOREIGN PATENT DOCUMENTS

| | | |
|---|---|---|
| JP | 2013007601 | 1/2013 |
| WO | 02/04929 | 1/2002 |
| WO | 2006/054116 | 5/2006 |
| WO | 2012160005 | 11/2012 |

OTHER PUBLICATIONS

Blatter et al., Dove prism based rotating dual beam bidirectional Doppler OCT, Biomedical Optics Express, vol. 4, No. 7 (Jul. 1, 2013), pp. 1188-1203.
Braff et al., Angiography of the retina and the choroid with phase-resolved OCT using interval-optimized backstitched B-scans, Optics Express, vol. 20, No. 18 (Aug. 27, 2012), pp. 20516-20534.
Chinn et al., Optical coherence tomography using a frequency-tunable optical source, Optics Letters, vol. 22, Issue 5 (Mar. 1, 1997), pp. 340-342.
Choi et al., Phase-sensitive swept-source optical coherence tomography imaging of the human retina with a vertical cavity surface-emitting laser light source, Optics Letters, vol. 38, Issue 3 (Feb. 1, 2013), pp. 338-340.
Fercher et al., Measurement of intraocular distances by backscattering spectral interferometry, Optics Communications, vol. 117, Issues 1-2 (May 15, 1995), pp. 43-48.
Hendargo et al., Doppler velocity detection limitations in spectrometer-based versus swept-source optical coherence tomography, Biomed. Opt. Express, vol. 2, No. 8 (Aug. 1, 2011), pp. 2175-2188.
Jaillon et al., Variable velocity range imaging of the choroid with dual-beam optical coherence angiography, Optics Express, vol. 20, No. 1 (Jan. 2, 2012), pp. 385-396.
Klein et al., Megahertz OCT for ultrawide-field retinal imaging with a 1050nm Fourier domain mode-locked laser, Optics Express, vol. 19, No. 4 (Feb. 14, 2011), pp. 3044-3062.
Makita et al., Dual-beam-scan Doppler optical coherence angiography for birefringence-artifact-free vasculature imaging, Optics Express, vol. 20, No. 3 (Jan. 30, 2012), p. 2681-2692.
Park et al., Double common-path interferometer for flexible optical probe of optical coherence tomography, Optics Express, vol. 20, No. 2 (Jan. 16, 2012), pp. 1102-1112.
Park et al., Real-time fiber-based multi-functional spectral-domain optical coherence tomography at 1.3µm, Optics Express, vol. 13, No. 11 (May 30, 2005), pp. 3931-3944.
Potsaid et al., Ultrahigh speed 1050nm swept source / Fourier domain OCT retinal and anterior segment imaging at 100,000 to 400,000 axial scans per second, Optics Express, vol. 18, No. 19 (Sep. 13, 2010), pp. 20029-20048.
Werkmeister et al., Bidirectional Doppler Fourier-domain optical coherence tomography for measurement of absolute flow velocities in human retinal vessels, Optics Letters, vol. 33, Issue 24 (Dec. 15, 2008), pp. 2967-2969.
Zhao et al., Doppler standard deviation imaging for clinical monitoring of in vivo human skin blood flow, Optics Letters, vol. 25, No. 18 (Sep. 15, 2000), pp. 1358-1360.
Zotter et al., Visualization of microvasculature by dual-beam phase-resolved Doppler optical coherence tomography, Optics Express, vol. 19, No. 2 (Jan. 17, 2011), pp. 1217-1227.
European Extended Search Report dated Mar. 23, 2015, issued in European Patent Application No. 14306748.6, 6 pages.
Nicusor V. Iftimia, et al., Dual-beam Fourier domain optical Doppler tomography of zebrafish, Optics Express, Sep. 1, 2008, pp. 13624-13636, vol. 16, No. 18.
Office Action dated Oct. 25, 2016 in corresponding Japanese Application No. 2014221411.
European Extended Search Report dated May 3, 2017 in the corresponding European Patent Application No. 17155412.4.

* cited by examiner

WAVELENGTH ENCODED MULTI-BEAM OPTICAL COHERENCE TOMOGRAPHY

CROSS-REFERENCE TO RELATED APPLICATIONS

The present application is a continuation of, and claims priority to U.S. patent application Ser. No. 14/925,993, titled "MULTI-CHANNEL OPTICAL COHERENCE TOMOGRAPHY," filed on Oct. 29, 2015, all of which is incorporated herein by reference in its entirety for all purposes, which is a continuation of, and claims priority to U.S. patent application Ser. No. 14/069,626, titled "MULTI-CHANNEL OPTICAL COHERENCE TOMOGRAPHY," filed on Nov. 1, 2013, all of which is incorporated herein by reference in its entirety for all purposes, and also claims the benefit of Japanese Patent Application No. 2014-221411 titled "MULTI-CHANNEL OPTICAL COHERENCE TOMOGRAPHY," filed on Oct. 30, 2014, all of which is incorporated herein by reference in its entirety for all purposes.

If any definitions (e.g., figure reference signs, specialized terms, examples, data, information, definitions, conventions, glossary, etc.) from any related material (e.g., parent application, other related application, material incorporated by reference, material cited, extrinsic reference, etc.) conflict with this application (e.g., abstract, description, summary, claims, etc.) for any purpose (e.g., prosecution, claim support, claim interpretation, claim construction, etc.), then the definitions in this application shall apply.

FIELD OF THE INVENTION

The present invention relates generally to the field of optical coherence tomography and, more particularly, to systems and methods for multi-channel wavelength encoded optical coherence tomography.

BACKGROUND

Various different methods have been published regarding multi-beam systems for optical coherence tomography ("OCT") that aim at absolute velocity measurement or contrast imaging enhancement of motion occurring inside a sample. In particular, these methods provide a non-invasive way of quantifying blood velocity and improving blood vessel visualizations for biological samples.

First, OCT techniques that provide absolute velocity measurements are typically based on laser Doppler velocimetry. Such techniques typically involve illuminating the sample at a given location, with beams having different incident angles. For example, in the case of spectral domain OCT, one approach is to use polarization multiplexing and a beam displacer to generate two beams, as shown by R. Werkmeister, et al., in "Bidirectional Doppler Fourier-domain optical coherence tomography for measurement of absolute flow velocities in human retinal vessels," Opt. Lett., Vol. 33, Issue 24 (2008), pp. 2967-2969. Similarly, using a knife edge mirror, two beams can be generated as shown by N. Iftimia et al., in "Dual-beam Fourier domain optical coherence tomography of zebrafish," Opt. Express, Vol. 16, No. 18 (2008), pp. 13624-13636. These techniques typically require two detectors for acquiring both signals.

Another approach is to encode the two beams with different path lengths, as demonstrated by Pedersen et al. in "Measurement of absolute flow velocity vector using dual-angle, delay-encoded Doppler optical coherence tomography," Opt. Lett., Vol. 32, No. 5 (2007), pp. 506-508. In this technique a glass plate is positioned midway into the OCT beam path. This technique has the advantage of using a single detector but has the disadvantage of dividing by three the depth range of acquired OCT signal. Additionally, in systems that use only two incident beams, the angle between the measured velocity vector and the plane formed by the two incident beams must be close to zero. If the angle is not close to zero, this method is prone to large velocity measurement errors.

Therefore, other techniques using three beams have been developed, such as, for example, W. Trasischker et al., in "In vitro and in vivo three-dimensional velocity vector measurement by three beam spectral-domain Doppler optical coherence tomography", J. Biomed. Opt., Vol. 18, No. 11, (2013), pp. 116010-1-116010-11. W. Trasischker et al. utilized three sources and three detectors in the case of spectral domain OCT.

Second, OCT techniques that provide imaging contrast enhancement of motion inside a sample are typically performed with two scanning beams having the same incident angle on the sample. This technique typically involves scanning the sample such that the two beams scan the same location at two different instants. Depending on the delay between the two instants, the motion contrast can be modified. Typically, slow motion is better visualized with a larger delay. Such techniques provide, in living tissues for example, image of blood vessels, namely angiographies.

Various different OCT methods have been published for generating and acquiring the two beams. For example, methods with polarization multiplexing have been demonstrated by Makita et al., in "Dual-beam-scan Doppler optical coherence angiography for birefringence-artifact-free vasculature imaging," Opt. Express, Vol. 20, No. 3 (2012), pp. 2681-2692 (US Patent US20120120408 A1). In that method, one light source and two detectors were used. However, issues with the sample birefringence may cause contrast deterioration. Another variant uses non-polarizer elements, such as shown by S. Zotter, et al., in "Visualization of microvasculature by dual-beam phase-resolved Doppler optical coherence tomography," Opt. Express, Vol 19, No. 2 (2011), pp. 1217-1227. But in this case, significant losses of the signal exist. Moreover, the previous method was performed with two sources and two detectors, increasing cost and complexity.

Another approach for generating two beams from a single light source involves encoding each beam with a free-space acousto-optic frequency shifter, as demonstrated by S. Kim et al., "Multi-functional angiographic OFDI using frequency-multiplexed dual-beam illumination", Opt. Express, Vol. 23, No. 07 (2015), pp. 8939-8947. One disadvantage of this method is the limitation of the distance between beams on the sample due to limited optical bandwidth of the frequency shifter for larger beams.

Therefore, there is a need for a system and/or method for optical coherence tomography that addresses at least some of the problems and disadvantages associated with conventional systems and methods.

SUMMARY

The following summary is provided to facilitate an understanding of some of the innovative features unique to the embodiments disclosed and is not intended to be a full description. A full appreciation of the various aspects of the embodiments can be gained by taking into consideration the entire specification, claims, drawings, and abstract as a whole.

In one aspect, an optical coherence tomography apparatus includes a first electro-magnetic radiation (EMR) source provides EMR to a first optical path and a second optical path, wherein the first optical path is associated with a sample and the second optical path is associated with a reference. A multi-beam generator unit (MBGU) couples to the first optical path and a scanning system. The MBGU generates a first EMR beam and a second EMR beam, the first EMR beam having different wavelength contents than the second EMR beam. The MBGU provides the first EMR beam and the second EMR beam to the scanning system. The scanning system illuminates the sample with the first EMR beam and the second EMR beam, at a first time and a second time, at a first location and a second location of the sample, the second location being near to the first location. In one embodiment, the second location is near to the first location when the EMR beams illuminating the first and second location are at least partially overlapping. An interference module couples to the first optical path and the second optical path. The interference module generates interference signals based on received EMR returning from the reference and the first EMR beam and the second EMR beam returning from the sample. A detector coupled to the interference module generates detection signals based on received interference signals. A processor coupled to the detector processes detection signals received from the detector and generates optical coherence tomography data based on the processed detection signals.

In one embodiment, the MBGU generates the first EMR beam and the second EMR beam to comprise variable relative directions. In one embodiment, the scanning system comprises a pivot point and the MBGU provides the first EMR beam and the second EMR beam so as to intersect with the pivot point. In one embodiment, generating the first EMR beam and the second EMR beam to comprise variable relative directions comprises manipulating optical components including at least one of the following: selecting or moving one of the plurality of optical paths wherein each optical paths comprises a dedicated optical fiber; a fiber Bragg grating, a blazed grating; a dispersive medium; an optical switch; a dichroic mirror; a wavelength division multiplexer; and moving a mirror to change relative directions or distances between the first EMR beam and the second EMR beam.

In one embodiment, the MBGU generates the first EMR beam and the second EMR beam to comprise overlapping wavelength contents. In one embodiment, the MBGU generates the first EMR beam and the second EMR beam without regard to a polarization relationship between the first EMR beam and the second EMR beam. In one embodiment, the optical coherence tomography data comprises at least one of the following: a phase difference; an absolute phase difference; a square of the phase difference; a phase variance; an amplitude decorrelation and a speckle decorrelation between at least two complex OCT signals originating from the second location.

In one embodiment, the processor reduces motion artifacts. In one embodiment, the first optical path and the second optical path share common optical components. In one embodiment, the processor compares at least two complex OCT signals originating from the second location.

In another aspect, an optical coherence tomography method includes providing electro-magnetic radiation (EMR) to a first optical path and a second optical path, wherein the first optical path is associated with a sample and the second optical path is associated with a reference. A first EMR beam and a second EMR beam are generated, the first EMR beam having different wavelength contents than the second EMR beam. The first EMR beam and the second EMR beam are provided to a scanning system. The sample is illuminated with the first EMR beam and the second EMR beam, at a first time and a second time, at a first location and a second location of the sample, the second location being near to the first location. In one embodiment, the second location is near to the first location when the EMR beams illuminating the first and second location are at least partially overlapping. Interference signals are generated based on received EMR returning from the reference and the first EMR beam and the second EMR beam returning from the sample. Detection signals are generated based on the interference signals. Detection signals are processed to generate optical coherence tomography data based on the processed detection signals.

In another aspect an optical coherence tomography apparatus includes a first electro-magnetic radiation (EMR) source provides EMR to a first optical path and a second optical path, wherein the first optical path is associated with a sample and the second optical path is associated with a reference. A multi-beam generator unit (MBGU) couples to the first optical path and a scanning system. The MBGU generates a first EMR beam, a second EMR beam, and a third EMR beam, the first EMR beam, the second EMR beam, and the third EMR beam having different wavelength contents. The MBGU being further provides the first EMR beam, the second EMR beam, and the third EMR beam to the scanning system. The scanning system illuminates the sample with the first EMR beam, the second EMR beam, and the third EMR beam such that, at the sample surface, the first EMR beam, the second EMR beam, and the third EMR beam comprise linearly independent vectors. An interference module coupled to the first optical path and the second optical path. The interference module generates interference signals based on received EMR returning from the reference and the first EMR beam, the second EMR beam, and the third EMR beam returning from the sample. A detector coupled to the interference module generates detection signals based on received interference signals. A processor coupled to the detector processes detection signals received from the detector and generates optical coherence tomography data based on the processed detection signals.

In one embodiment, the MBGU generates the first EMR beam, the second EMR beam, and the third EMR beam to comprise variable relative distances. In one embodiment, the MBGU generates the first EMR beam, the second EMR beam, and the third EMR beam by manipulating optical components including at least one of the following: one of a plurality of optical paths wherein each optical path comprises a dedicated optical fiber; a fiber Bragg grating, a blazed grating; a dispersive medium; an optical switch; a dichroic mirror; a wavelength division multiplexer; and a mirror. In one embodiment, the MBGU generates the first EMR beam, the second EMR beam, and the third EMR beam to comprise overlapping wavelength contents.

In one embodiment, the MBGU generates the first EMR beam, the second EMR beam, and the third EMR beam without regard to a polarization relationship between the first EMR beam, the second EMR beam, and the third EMR beam. In one embodiment, the processor calculates at least three phase differences of at least six complex OCT signals originating from at least one nearby position on the sample. In one embodiment, a position is nearby on the sample when the EMR beams illuminating the sample at a given position are at least partially overlapping. In one embodiment, the processor reduces motion artifacts. In one embodiment, the first optical path and the second optical path share common optical components.

In another aspect, an optical coherence tomography method includes providing electro-magnetic radiation (EMR) to a first optical path and a second optical path, wherein the first optical path is associated with a sample and the second optical path is associated with a reference. A first EMR beam, a second EMR beam, and a third EMR beam are generated, the first EMR beam, the second EMR beam, and the third EMR beam having different wavelength contents. The first EMR beam, the second EMR beam, and the third EMR beam are provided to a scanning system. The sample is illuminated with the first EMR beam, the second EMR beam, and the third EMR beam such that the first EMR beam, the second EMR beam, and the third EMR beam comprise linearly independent vectors. Interference signals are generated based on received EMR returning from the reference and the first EMR beam, the second EMR beam, and the third EMR beam returning from the sample. Detection signals are generated based on received interference signals. Detection signals received from the detector are processed and optical coherence tomography data are generated based on the processed detection signals.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DESCRIPTION OF THE PREFERRED EMBODIMENT(S)

Figure 1:
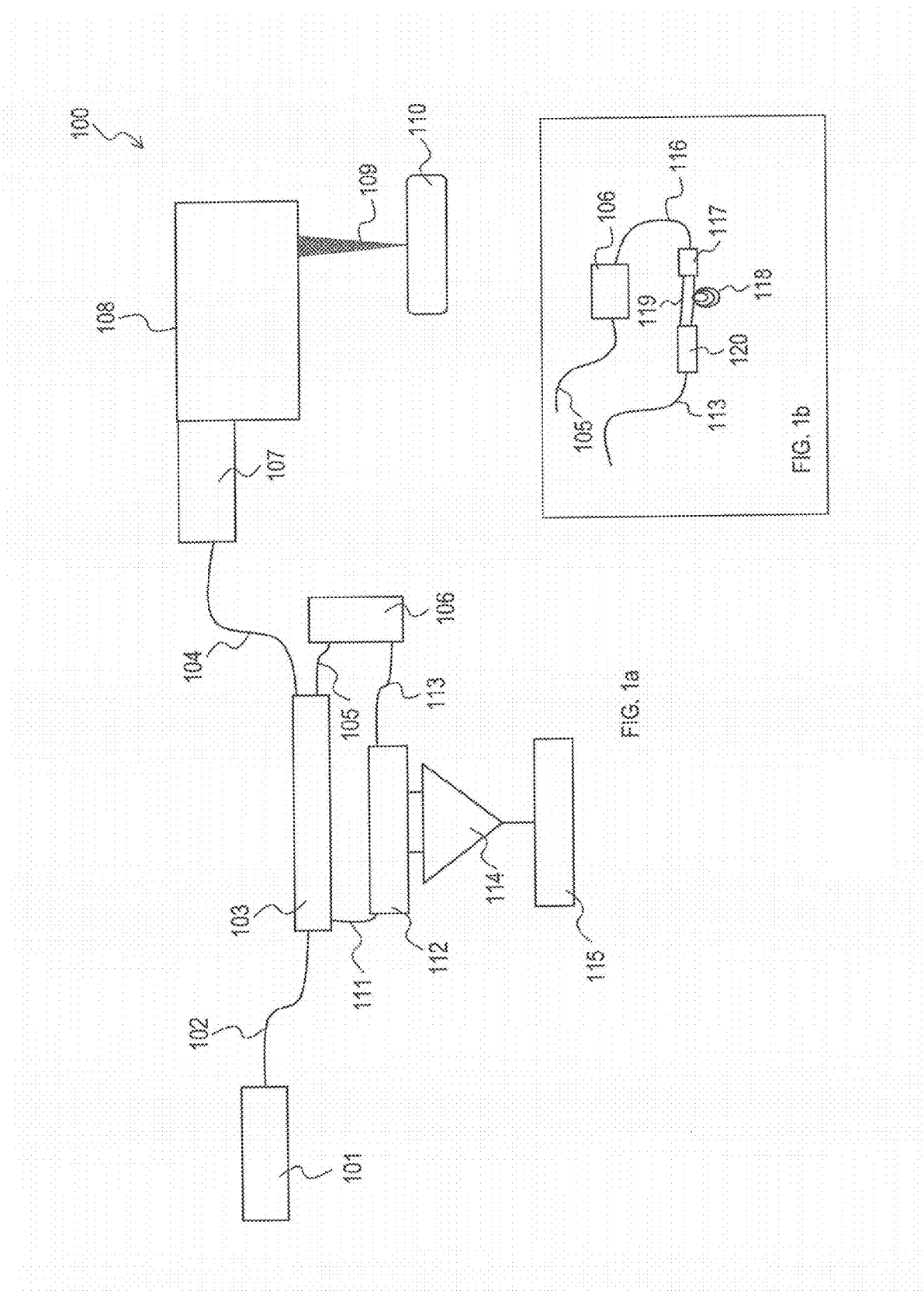
FIGS. 1a and 1b are block diagrams showing a multi-channel optical coherence tomography apparatus in accordance with one embodiment.

The particular values and configurations discussed in these non-limiting examples can be varied and are cited merely to illustrate at least one embodiment and are not intended to limit the scope of the invention.

In the following discussion, numerous specific details are set forth to provide a thorough understanding of the present invention. Those or ordinary skill in the art will appreciate that the present invention may be practiced without such specific details. In other instances, well-known elements have been illustrated in schematic or block diagram form in order not to obscure the present invention in unnecessary detail. Additionally, for the most part, details concerning routine operations or devices such as light sources, fiber coupling techniques, optical scanning techniques, and the like, have been omitted inasmuch as such details are not considered necessary to obtain a complete understanding of the present invention, and are considered to be within the understanding of persons of ordinary skill in the relevant art.

Generally, the various embodiments described herein provide technical advantages over legacy systems and method. For example, In accordance with exemplary embodiments of the present invention, a multi-beam optical coherence tomography (OCT) apparatus can provide incident beams with different wavelength contents in order to enhance motion imaging contrast and/or to measure absolute velocity of motions inside a sample under study. The disclosed embodiments can be applied, for example, to spectral domain OCT or swept-source OCT. In some embodiments, because each beam is encoded according to its wavelength bandwidth, the resulting interference signals can be detected by a single detection module. In the case of some spectral domain OCT embodiments, each beam is simultaneously detected. In the case of some swept-source OCT embodiments, detection is time dependent and therefore light source sweep speed should be configured to be smaller than motion speed inside the sample under the study. With such exemplary particular arrangements, a smaller wavelength bandwidth implies larger axial resolution.

However, in some embodiments, smaller wavelength bandwidths are only used for motion contrast and velocity measurements. In such embodiments, larger axial resolution is usually not an issue since these measurements typically involve depth averaging before display. Regarding the OCT structure imaging, for a given A-line, the axial resolution is not typically affected as long as the location is scanned by all the beams whose combination reconstitutes the full wavelength bandwidth.

According to one exemplary embodiment of the present invention, the optical coherence tomography system can be configured to implement a method to measure absolute velocity measurements inside a sample under study. In one embodiment a multi-beam generator is configured to generate three beams with different wavelength bandwidths. In one embodiment, the beams are generated by positioning two dichroic mirrors in series. In one embodiment, the two dichroic mirrors have different reflection and transmission properties such that the original wavelength bandwidth is split into three beams with different sub-bandwidths. In one embodiment, these three beams are non-coplanar and are directed along a same direction onto a scanning system. In one embodiment, an optical system following the multi-beam generator and the scanning system allows focusing these beams onto the sample. Generally, back-reflected lights from the sample interfere with a reference light and the interference signal is detected by a detection module. In one embodiment, comparing the complex OCT signals between the three detected interference signals and knowing the directions of these three beams in a reference frame allow the measurement of absolute velocity of motions inside the sample.

According to another exemplary embodiment of the present invention, the optical coherence tomography system can be configured to implement a method to measure absolute velocity measurements inside a sample under study. In one embodiment a multi-beam generator is configured to generate three beams with different wavelength bandwidths. In one embodiment, three dichroic mirrors are positioned perpendicularly to an incoming beam and positioned at different positions such that output transmitted beams do not overlap between each other. In one embodiment, the three dichroic mirrors have different reflection and transmission properties such that the original wavelength bandwidth is split into three beams with different sub-bandwidths. In one embodiment, these three beams are directed along a same direction onto a scanning system and are non-coplanar. In one embodiment, an optical system following the multi-beam generator and the scanning system allows focusing these beams onto the sample. Generally, back-reflected lights from the sample interfere with a reference light and the interference signal is detected by a detection module. In one embodiment, comparing the complex OCT signals between the three detected interference signals and knowing the directions of these three beams in a reference frame allow the measurement of absolute velocity of motions inside the sample.

According to one exemplary embodiment of the present invention, the optical coherence tomography system can be configured to implement a method to enhance motion contrast imaging inside a sample under study. In one embodiment is a multi-beam generator is configured to generate two beams with different wavelength bandwidths. In one embodiment, the beams are generated by a dichroic mirror. In one embodiment, by means of optical components, these two beams intersect at the pivot point of a scanning system following the multi-beam generator. In one embodiment, the multi-beam generator is configured to enable altering the angle between these beams on the scanning system by translating the two beams. In one embodiment, an optical system following the multi-beam generator and the scanning system allows focusing these beams onto the sample. In one embodiment, as the multi-beam generator alters the incident angle onto the scanning system, distance between beams on the sample is modified. In one embodiment, for a given scanned position on the sample, these beams impinge with a similar incidence angle but at different instants. In one embodiment, back-reflected lights from the sample interfere with a reference light and the interference signal is detected by a detection module. In one embodiment, comparing the complex OCT signals between the two detected interference signals allows motion contrast enhancement.

According to one exemplary embodiment of the present invention, the optical coherence tomography system can be configured to implement a method to enhance motion contrast imaging inside a sample under study. In one embodiment, a multi-beam generator is configured to generate two beams with different wavelength bandwidths. In one embodiment, the beams are generated by a dichroic mirror.

In one embodiment, by means of optical components, these two beams intersect at the pivot point of a scanning system following the multi-beam generator. In one embodiment, the multi-beam generator is configured to enable altering the angle between these beams on the scanning system by rotating the two beams. In one embodiment, an optical system following the multi-beam generator and the scanning system allows focusing these beams onto the sample. In one embodiment, as the multi-beam generator alters the incident angle onto the scanning system, distance between beams on the sample is modified. In one embodiment, for a given scanned position on the sample, these beams impinge with a similar incidence angle but at different instants. In one embodiment, back-reflected lights from the sample interfere with a reference light and the interference signal is detected by a detection module. In one embodiment, comparing the complex OCT signals between the two detected interference signals allows motion contrast enhancement.

According to one exemplary embodiment of the present invention, the optical coherence tomography system can be configured to implement a method to enhance motion contrast imaging inside a sample under study. In one embodiment a multi-beam generator is configured to generate two beams with different wavelength bandwidths. In one embodiment, the beams are generated by a dichroic mirror. In one embodiment, by means of optical components, these two beams intersect at the pivot point of a scanning system following the multi-beam generator. In one embodiment, the multi-beam generator is configured to enable altering the angle between these beams on the scanning system by rotating one beam and keeping fixed the other beam. In one embodiment, an optical system following the multi-beam generator and the scanning system allows focusing these beams onto the sample. In one embodiment, as the multi-beam generator alters the incident angle onto the scanning system, distance between beams on the sample is modified. In one embodiment, for a given scanned position on the sample, these beams impinge with a similar incidence angle but at different instants. In one embodiment, back-reflected lights from the sample interfere with a reference light and the interference signal is detected by a detection module. In one embodiment, comparing the complex OCT signals between the two detected interference signals allows motion contrast enhancement.

Turning now to various specific embodiments, FIG. 1 is a block diagram showing a multi-channel optical coherence tomography apparatus in accordance with one embodiment. More specifically, FIGS. 1a and 1b are a high-level block diagrams illustrating certain components of a system 100 for multi-channel optical coherence tomography, in accordance with a preferred embodiment of the present invention. Generally, in the illustrated embodiment, system 100 is configured to perform multi-beam OCT with one detection unit, providing a plurality of electro-magnetic radiation (EMR) beams onto a sample, where each EMR beam has different wavelength content. In the following descriptions, one having ordinary skill in the art will understand that systems that allow the synchronization between the light source, the scanning system, the optical switch, and the detection have been omitted for ease of discussion.

One of ordinary skill in the art will understand that light is a form of EMR and that OCT techniques typically use beams of light. For ease of description, EMR is sometimes described herein as "light," or a "beam," and sometimes as a "light beam." One of ordinary skill in the art will understand that the properties of EMR are complex and the use of the terms "light," "beam," or "light beam" is not intended to limit the disclosed electro-magnetic radiation in any way, such as in terms of quantity, intensity, wavelength, etc.

In one embodiment, a first EMR beam has "different wavelength content" from a second EMR beam when the range of wavelengths of the first EMR beam does not overlap with the range of wavelengths in the second EMR beam. In one embodiment, a first EMR beam has "different wavelength content" from a second EMR beam when the first EMR beam comprises wavelengths that include some, but not all, wavelengths of the second EMR beam.

FIG. 1a is a block diagram showing a multi-channel OCT system 100 in accordance with one embodiment. In the illustrated embodiment, system 100 includes an EMR source 101. In the illustrated embodiment, EMR source 101 is a light source configured to generate light having a wavelength bandwidth $\Delta\lambda$. In an alternate embodiment, EMR source 101 is configured to sweep in time wavelengths over bandwidth $\Delta\lambda$.

In the illustrated embodiment, an otherwise conventional optical fiber 102 couples to EMR source 101 and a fiber coupler 103. In the illustrated embodiment, fiber coupler 103 is an otherwise conventional fiber coupler and splits light from EMR source 101 into two paths: a sample arm (beginning with fiber 104) and a reference arm (beginning with fiber 105). One of ordinary skill in the art will understand that sample and reference arms are typical components of an interferometer and that different interferometer types can be used to perform OCT techniques, such as, for example, a Michelson type interferometer, a Mach-Zehnder interferometer, or a Fizeau type interferometer.

In the illustrated embodiment, light in the reference arm passes through a delay line 106. One of ordinary skill in the art will understand that there are various techniques available to produce a delay line, such as a simple length of coiled fiber, for example. Generally, a single reference arm with a single delay line typically generates a single reference signal. In one embodiment, system 100 is configured to generate two reference signals.

For example, as shown in FIG. 1b, in one embodiment, system 100 is configured to generate two reference signals with two different path-lengths. One having ordinary skill in the art will appreciate that generating two reference signals having different path lengths can help reduce or avoid cross-talk between the plurality of beams when the reference signal path-length difference is larger than the coherence length of light. In the illustrated embodiment, an otherwise conventional fiber 116 guides light exiting delay line 106 to an otherwise conventional fiber coupler 117. Fiber coupler 117 splits the received light into two paths: fiber 118 and fiber 119. As shown in the illustrated embodiment, fiber 118 and fiber 119 are configured with different lengths. Both fiber 118 and fiber 119 connect to a fiber coupler 120. As in FIG. 1a, fiber coupler 120 connects to fiber 113. Light from fiber 113 connects to the otherwise conventional fiber coupler 112, which also receives light returning from the sample, as described in more detail below.

In the sample arm, as shown in FIG. 1a, fiber 104 connects fiber coupler 103 to a multi-beam generator unit (MBGU) 107. Generally, in the illustrated embodiment, MBGU 107 generates, from light received from fiber 104, a plurality of beams distinguishable from each other by their wavelength content. That is, in one embodiment, each generated beam will comprise light have a plurality of wavelengths, thus comprising that beam's "wavelength contents." In one embodiment, the wavelength contents of the generated beams do not overlap. In one embodiment, wherein MBGU 107 comprises band pass filters, the wavelength contents of the generated beams include some overlapping bandwidths. In one embodiment, the wavelength contents are sufficiently different that the number of overlapping bandwidths does not significantly impair OCT accuracy.

In the illustrated embodiment, the generated beams from MBGU 107 are directed into a scanning unit 108. Generally, scanning unit 108 illuminates the sample and collects light returning from the sample. As shown in the illustrated embodiment, scanning unit 109 focuses the plurality of beams 109 and scans sample 110. As described in more detail below, depending on the MBGU 107 configuration, the directions and locations of the beams 109 illuminating sample 110 can be adjusted.

One having ordinary skill in the art will understand that light from beams 109 is back-reflected by the sample 110. Scanning unit 108 receives the back-reflected light returning from sample 110 and directs the returning light to the MBGU 107. As shown in the illustrated embodiment, MBGU 107 redirects returning light to coupler 103 via fiber 104. Fiber coupler 103 directs returning light to fiber coupler 112 via fiber 111.

As described above, fiber coupler 112 also receives light from the reference arm. As such, in the illustrated embodiment, light from the reference arm and light returning from the sample interfere in coupler 112, thereby generating interference signals. Generally, in the illustrated embodiment, the interference signal is acquired as a function of the wavelength, wherein different wavelength bandwidths correspond to different beams. A detection module 114 coupled to coupler 112 detects the interference signals, and generates detection signals. A processing unit 115 coupled to detection module 114 processes received detection signals, thereby generating OCT data (or passing processed detection signals on for further processing into OCT data) that can subsequently be organized, transformed, etc. for presentation to a user, in many cases as an image. One having ordinary skill in the art will appreciate that interference signals, detection signals, and processing can be achieved in a variety of ways, customizable depending on the desired application, general sample characteristics, use environment, etc.

Generally, as used herein, a "processing unit" or "processing system" is a collection of one or more components configured to OCT analysis based on received input. In one embodiment, a processing system is configured to perform OCT motion analysis, which one of ordinary skill in the art will understand to be analysis of the velocity (relative or absolute) of particles inside the sample. In one embodiment, a processing system is further configured to perform volumetric or structural analysis, which one of ordinary skill in the art will understand to be analysis of the physical structure and/or volume of the sample.

Figure 2:
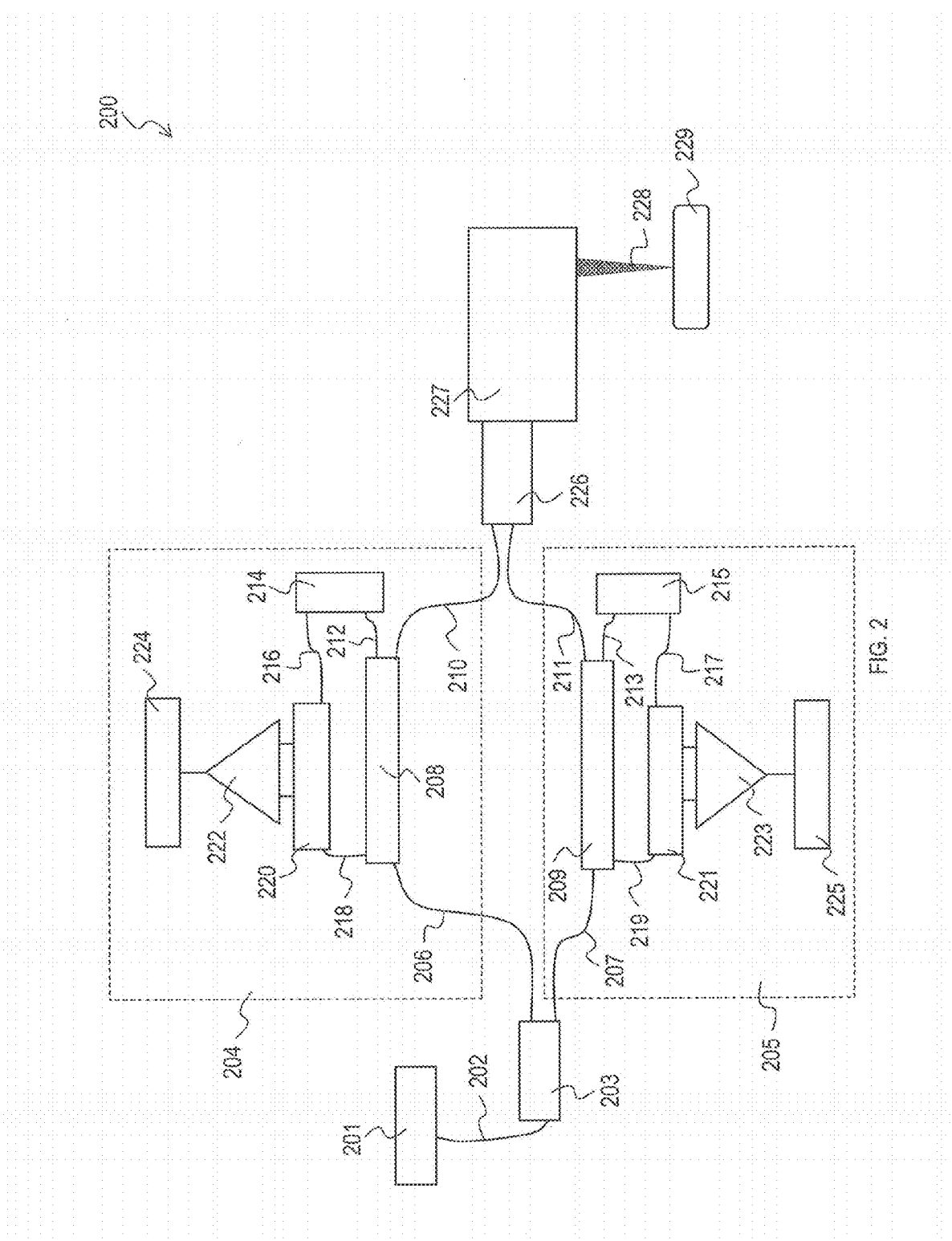
FIG. 2 is a block diagram showing a multi-channel optical coherence tomography apparatus in accordance with another embodiment.

The embodiments illustrated in FIGS. 1a and 1b include a single detector. In an alternate embodiment, multiple detectors can also be employed. For example, FIG. 2 is a block diagram showing a multi-channel OCT apparatus in accordance with a two-detector embodiment. Specifically, FIG. 2 shows a multi-channel OCT system 200 that includes multiple detectors. Specifically, system 200 can be configured for multi-beam OCT with two detection units, providing onto a sample multiple beams having different wavelength content. One having ordinary skill in the art will understand that using two interferometers and different fiber lengths improves decreasing the effect of cross-talk noise between the measured OCT signals.

As shown in the illustrated embodiment, system 200 includes EMR source 201. As with EMR source 101, EMR source 201 can also be configured in a variety of embodiments, including generating light that has, or that sweeps in time, a wavelength bandwidth Δλ. In the illustrated embodiment, a fiber 202 delivers light to an otherwise conventional fiber coupler 203. Fiber coupler 203 directs received light into interferometer 204 and interferometer 205. As with previous embodiments, one of ordinary skill in the art will understand that different interferometer types can be used to perform OCT techniques, such as, for example, a Michelson type interferometer, a Mach-Zehnder interferometer, or a Fizeau type interferometer.

In the illustrated embodiment, interferometers 204 and 205 are substantially similar. In alternate embodiments, interferometers 204 and 205 can be configured with, for example, different optical components, interference/detection/processing techniques, operating parameters, etc. For ease of discussion, interferometers 204 and 205 will be described as having similar characteristics.

In the illustrated embodiment, fiber 206 (207), of interferometer 204 (205), conveys light to a fiber coupler 208 (209). Fiber coupler 208 (209) splits light into a sample arm (fiber 210 (211)) and a reference arm (fiber 212 (213)). In the illustrated embodiment, light in the reference arm 212 (213) passes through a delay line 214 (215). Reference light exiting delay line 214 (215) is directed via fiber 216 (217) to fiber coupler 220 (221).

In the illustrated embodiment, the sample arm fiber 210 (211) directs received light from fiber coupler 208 (209) to a joint multi-beam generator unit (MBGU) 226. MBGU 226 generates, from the light received from fibers 210 and 211, a plurality of beams distinguishable by their wavelength content. In the illustrated embodiment, the generated beams from MBGU 226 are directed into a scanning unit 227. Generally, scanning unit 227 illuminates the sample and collects light returning from the sample. As shown in the illustrated embodiment, scanning unit 227 focuses the plurality of beams 228 and scans sample 229. As described in more detail below, depending on the MBGU 226 configuration, the directions and locations of the beams 228 illuminating sample 229 can be adjusted.

One having ordinary skill in the art will understand that light from beams 228 is back-reflected by the sample 229. Scanning unit 227 receives the back-reflected light returning from sample 229 and directs the returning light to the MBGU 226 and then to interferometers 204 (205). As shown in the illustrated embodiment, MBGU 226 redirects returning light to coupler 208 (209) via fiber 210 (211). Fiber coupler 208 (209) directs returning light to fiber coupler 220 (221) via fiber 218 (219).

As described above, fiber coupler 220 (221) also receives light from the corresponding reference arm. As such, in the illustrated embodiment, light from the corresponding reference arm and light returning from the sample interfere in coupler 220 (221), thereby generating interference signals. Generally, in the illustrated embodiment, the interference signal is acquired as a function of the wavelength, wherein different wavelength bandwidths correspond to different beams. A detection module 222 (223) coupled to coupler 220 (221) detects the interference signals, and generates detection signals. A processing unit 224 (225) coupled to detection module 222 (223) processes received detection signals, thereby generating OCT data.

Figure 3:
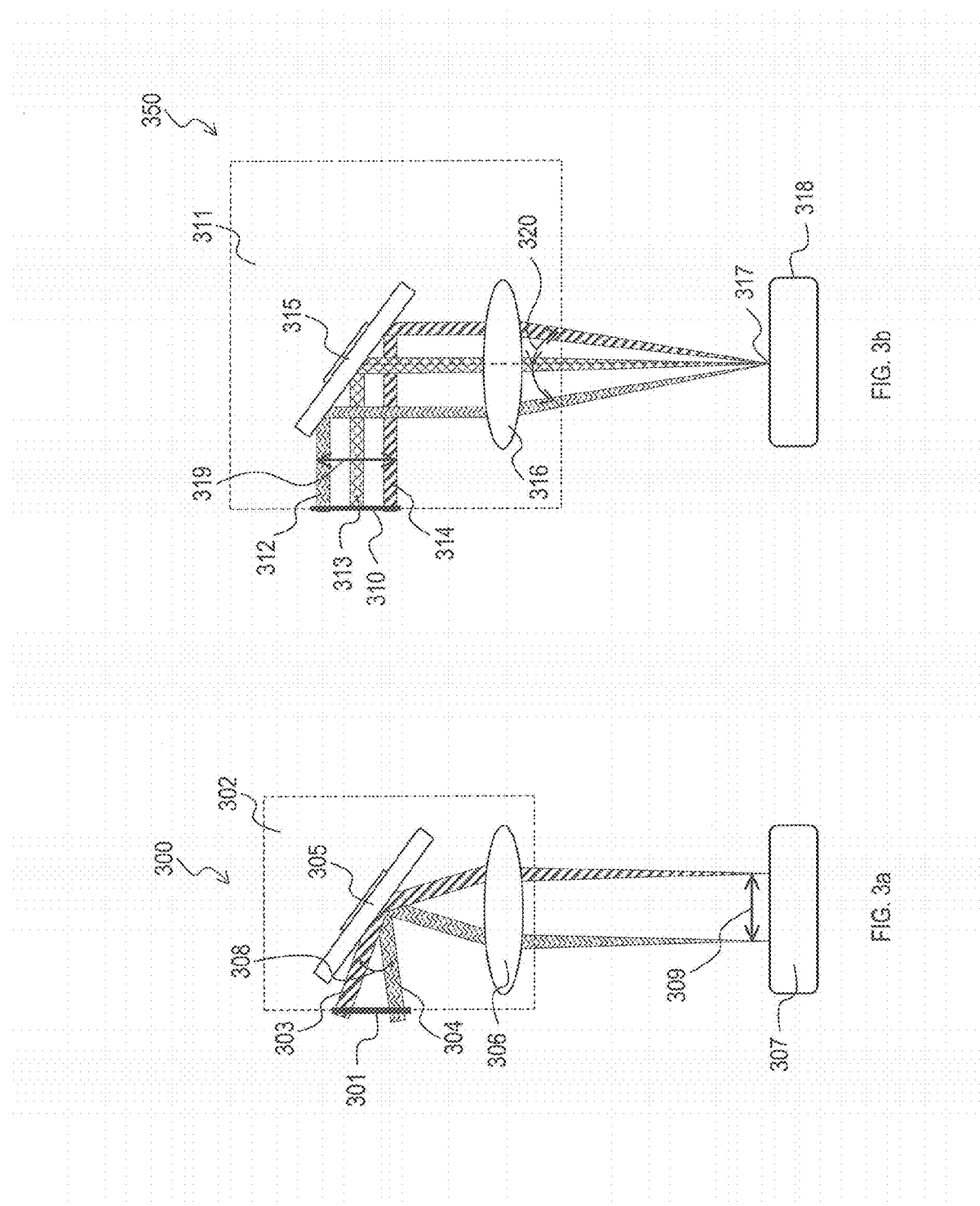
FIGS. 3a and 3b are block diagrams showing two scanning types with a plurality of beams, in accordance with one embodiment.

As described above, systems 100 and 200 can be configured to illuminate the sample in a variety of configurations. FIGS. 3a and 3b illustrate two such configurations, each using a plurality of beams.

FIG. 3a is a block diagram showing a MBCU/scanning unit in accordance with one embodiment. More particularly, FIG. 3a illustrates a system 300 configured to deliver light beams having the same incident angle when scanning the same position of the sample. In FIG. 3a, light beams from an associated MBGU enter a scanning unit 302 at interface 301. In the illustrated embodiment, two beams (303, 304) enter the scanning unit 302.

In the illustrated embodiment, scanning unit 302 includes a scanning mirror 305 and a lens 306. One having ordinary skill in the art will understand that other configurations, including more complex systems, can also be employed. In the illustrated embodiment, beams 303 and 304 intersect on scanning mirror 305 and are reflected towards the lens 306. Lens 306 focuses the beams onto a sample 307.

In the illustrated embodiment, by changing the intersection angle 308 between beams 303 and 304, the distance 309 between beams (at their focusing positions on sample 307) can be adjusted. As the beams 303 and 304 are transversally scanned onto sample 307, the delay between beams to scan the same position on the sample depends on the scanning speed and the distance 309. One having ordinary skill in the art will understand that this adjustable delay can be used in Doppler OCT to contrast motions inside the sample. For example, increasing the delay generally improves observation of slower motions in the sample.

FIG. 3b is a block diagram showing a MBGU/scanning unit in accordance with one embodiment. More particularly, FIG. 3b illustrates a system 350 configured to deliver light beams that impinge onto the sample at the same location with different incident angles. In FIG. 3b, light beams from an associated MBGU enter a scanning unit 311 at interface 310. In the illustrated embodiment, three beams (312, 313, and 314) enter the scanning unit 311.

In the illustrated embodiment, scanning unit 311 includes a scanning mirror 315 and a lens 316. One having ordinary skill in the art will understand that other configurations, including more complex systems, can also be employed. In the illustrated embodiment, beams 312, 313 and 314 impinge on the scanning mirror 315 in parallel directions and are reflected towards the lens 316. Lens 316 focuses the beams at a given location 317 onto a sample 318.

In the illustrated embodiment, by changing the distances between beams 312, 313 and 314, the incident angles 320 between the beams at focusing position 317 on sample 318 can be adjusted. One having ordinary skill in the art will understand that combining the OCT signals originating from the beams 312, 313 and 314, and the knowledge of the incident beam geometry, provides the absolute velocity of motions inside the sample.

Figure 4:
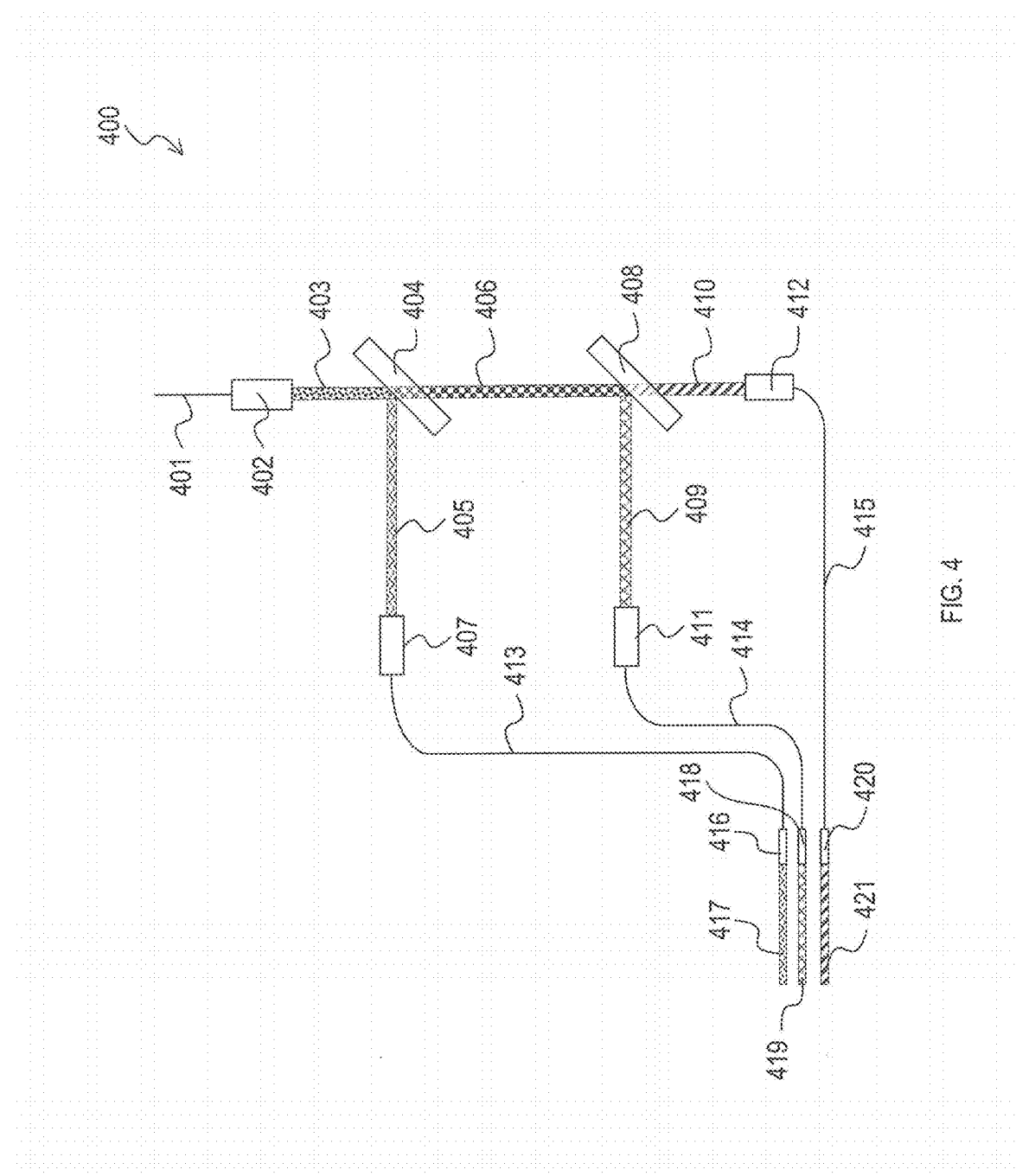
FIG. 4 is a block diagram showing a multi-beam generator unit in accordance with one embodiment.

FIG. 4 is a block diagram showing a multi-beam configuration unit in accordance with another embodiment. More particularly, FIG. 4 illustrates an MBGU 400 suitable for use as, for example, MBGU 107 of FIG. 1a.

In the illustrated embodiment, fiber 401 corresponds to, for example, fiber 404 of FIG. 1a. As shown in the illustrated embodiment, fiber 401 directs light to a collimator 402, which generates a beam 403. In the illustrated embodiment, the beam 403 wavelength contents comprise a wavelength bandwidth A. In the following, it is assumed that wavelength bandwidth Δλ can be decomposed into three sub bandwidths $\Delta\lambda_1$, $\Delta\lambda_2$ and $\Delta\lambda_3$, such as, for example, $\Delta\lambda_1 \leq \Delta\lambda_2 \leq \Delta\lambda_3$.

In the illustrated embodiment, beam 403 hits a dichroic mirror 404. In the illustrated embodiment, dichroic mirror 404 reflects beam 405 (having wavelength bandwidth $\Delta\lambda_1$) and transmits beam 406 (having wavelength bandwidths $\Delta\lambda_2$ and $\Delta\lambda_3$). A collimator 407 collects beam 405, directing the light from beam 405 along fiber 413 to collimator 416.

In the illustrated embodiment, beam 406 hits a dichroic mirror 408. In the illustrated embodiment, dichroic mirror 408 reflects beam 409 (having wavelength bandwidth $\Delta\lambda_2$) and transmits beam 410 (having wavelength bandwidth $\Delta\lambda_3$). A collimator 411 collects beam 409, directing the light from beam 409 along fiber 414 to collimator 418. A collimator 412 collects beam 410, directing the light from beam 410 along fiber 415 to collimator 420. One having ordinary skill in the art will appreciate that other configurations can also be used to generate beams 405, 409, and 410, such as, for example, using directly output beams 405, 409 and 410 with additional optical elements.

In the illustrated embodiment, the outputs beams 417, 419, and 421, each having different wavelength contents, are directed onto a scanning unit (not shown), such as scanning unit 108 of FIG. 1*a*, for example. One having ordinary skill in the art will appreciate that these three beams will ordinarily have parallel directions before hitting at three different locations of the scanning unit, for example, as shown in FIG. 3*b*. Moreover, in the illustrated embodiment, the three are linearly independent before impinging upon the sample. In the illustrated embodiment, adjusting the length of fibers 413, 414, and 415 allows a user to change the optical path of each output beam. One having ordinary skill in the art will appreciate that this configuration can be employed to help reduce or remove cross-talks between beams 417, 419 and 421.

For example, assuming that using dichroic mirrors (404, 408) there are wavelength overlaps between $\Delta\lambda_1$ and $\Delta\lambda_2$ and between $\Delta\lambda_2$ and $\Delta\lambda_3$, but that there is no overlap between $\Delta\lambda_1$ and $\Delta\lambda_3$. One having ordinary skill in the art will understand that these relationships depend on the transition slope between transmission and reflection of the dichroic mirrors. Consequently, cross-talks between beams 417 and 419 or between beams 419 and 421 might exist, but cross-talks between 417 and 421 can be expected to be negligible.

As such, the path-lengths of beams 417 and 421 can be adjusted to be similar (or at least having a path-length difference less than the coherence length) to each other (changing fiber lengths of fibers 413 and 415 for example) and to be different from the path-length of beam 419 (fiber 414). One having ordinary skill in the art will appreciate that using two different path-lengths for the sample beams requires two path-lengths for the reference light. One such embodiment has been described above with respect to FIG. 1*b*, for example. Moreover, one having ordinary skill in the art will also appreciate that these embodiments can be extended to provide more than two different path-lengths.

Figure 5:
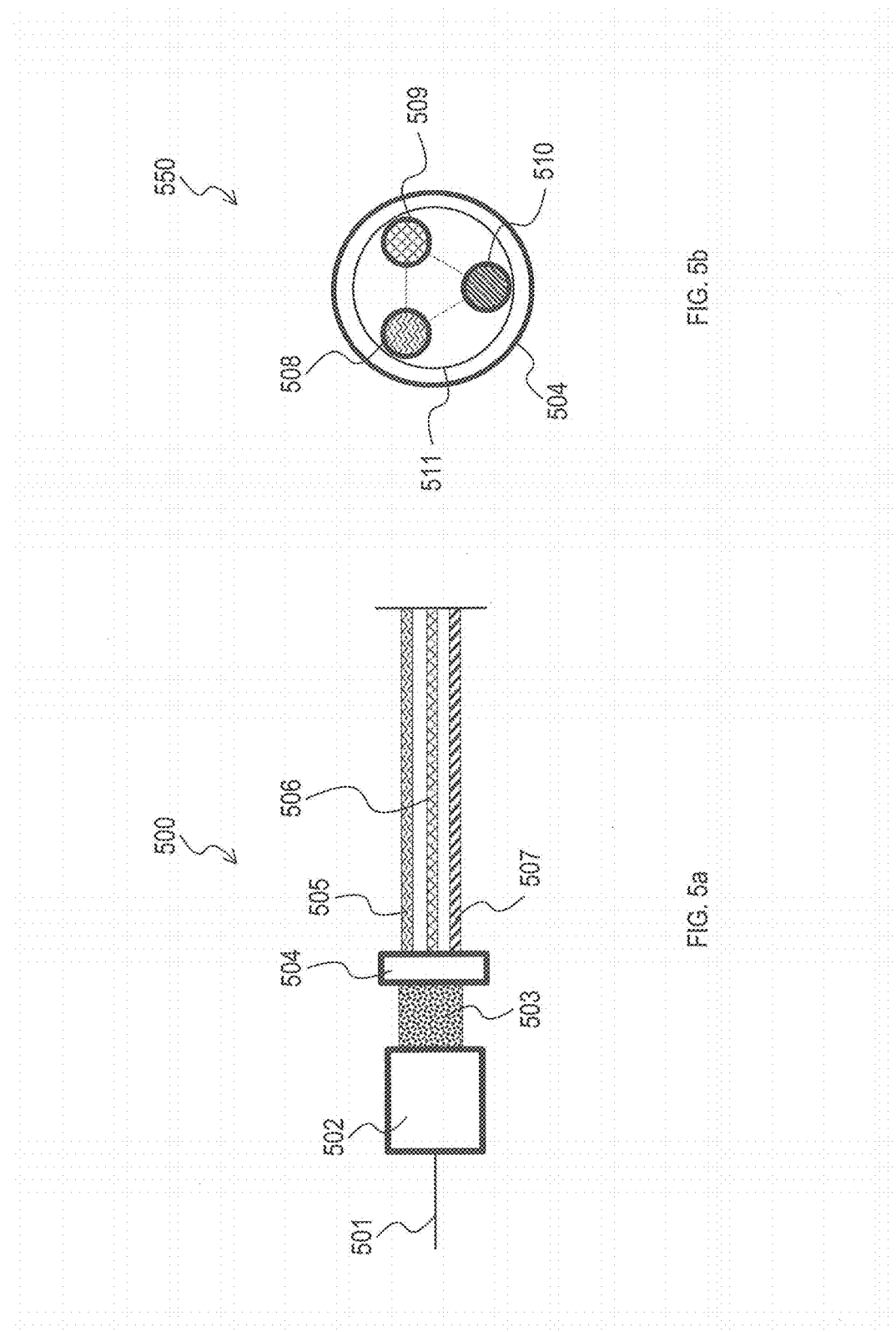
FIGS. 5a and 5b are block diagrams showing a multi-beam generator unit in accordance with another embodiment.

FIGS. 5*a* and 5*b* are block diagrams showing an MBGU in yet another embodiment. The embodiments shown in FIGS. 5*a* and 5*b* can be configured to serve as, for example, MGBU 107 in FIG. 1*a*. In the embodiment shown in FIG. 5*a*, MBGU 500 includes fiber 501. Fiber 501 corresponds to, for example, fiber 104 of FIG. 1*a*. As shown in the illustrated embodiment, fiber 501 connects to a collimator 502, which generates a beam 503. In the illustrated embodiment, beam 503 is configured with a wavelength bandwidth $\Delta\lambda$.

In the illustrated embodiment, beam 503 hits unit 504. In the illustrated embodiment, unit 504 is configured to transmit output beams 505, 506, and 507 such that output beams 505, 506, and 507 have different wavelength contents and different spatial locations. For example, in one embodiment, the wavelength bandwidths of output beams 505, 506, and 507 are $\Delta\lambda_1$, $\Delta\lambda_2$ and $\Delta\lambda_3$, respectively.

Generally, outputs beams 505, 506, and 507 are configured to be directed to a scanning system, such as, for example, scanning unit 108 of FIG. 1*a*. One having ordinary skill in the art will appreciate that these three output beams are typically linearly independent and typically have parallel directions before hitting at three different locations of the scanning system (e.g., as shown in FIG. 3*b*). Additional geometry of one embodiment is illustrated in FIG. 5*b*.

FIG. 5*b* displays a view 550 of unit 504 in the plane perpendicular to the propagation direction, in one embodiment. In the illustrated embodiment, unit 504 comprises three band-pass filters 508, 509, and 510. As described above, in one embodiment, the forward input path to unit 504 is beam 503, which comprises light having wavelength bandwidth $\Delta\lambda$. In the illustrated embodiment, band-pass filters 508, 509, and 510 transmit wavelength bandwidths $\Delta\lambda_1$, $\Delta\lambda_2$ and $\Delta\lambda_3$, respectively. As such, the output beams 505, 506, and 507 comprise light having wavelength bandwidths $\Delta\lambda_1$, $\Delta\lambda_2$ and $\Delta\lambda_3$, respectively, arranged in space according to the geometry of the band-pass filters in the illustrated embodiment.

One having ordinary skill in the art will also understand that this embodiment assumes that the incident power of the EMR/light source (e.g., EMR source 101) is high enough to tolerate losses in the forward path to the sample. For example, in the illustrated embodiment, if beam 503 is assumed circular with surface area given by surface area 511, losses in the forward path will be equal to the ratio between the surface area of the band-pass filters and the surface area 511. Accordingly, the EMR source can be configured to provide sufficient incident power to tolerate such losses. Moreover, one having ordinary skill in the art will appreciate that the backward path (light returning from the sample) is not affected by such losses.

Figure 6:
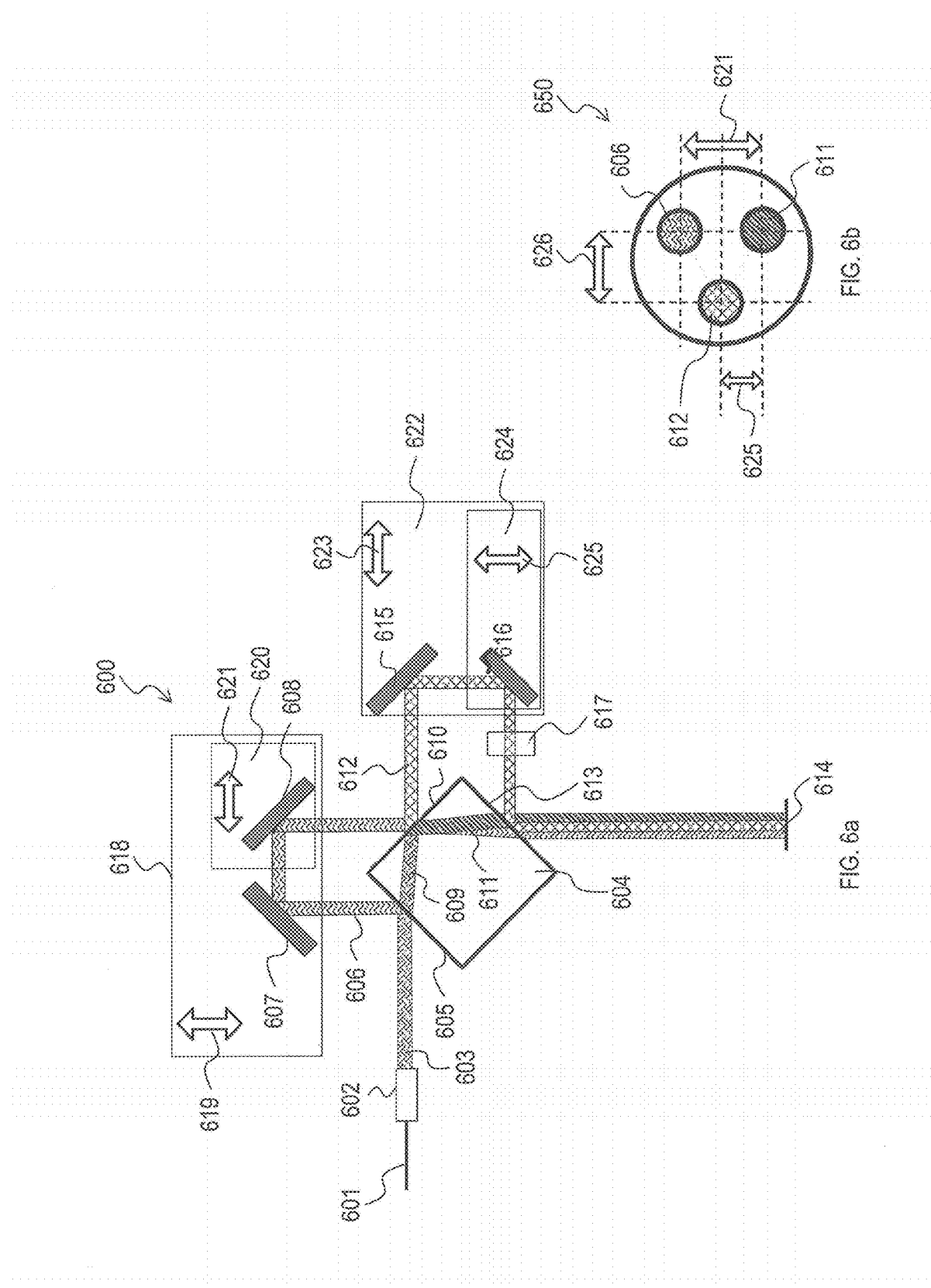
FIGS. 6a and 6b are block diagrams showing a multi-beam generator unit in accordance with yet another embodiment.

FIGS. 6*a* and 6*b* are block diagrams showing an MBGU in yet another embodiment. The embodiments shown in FIGS. 6*a* and 6*b* can be configured to serve as, for example, MGBU 107 in FIG. 1*a*. In the embodiment shown in FIG. 6*a*, MBGU 600 includes fiber 601. Fiber 601 corresponds to, for example, fiber 104 of FIG. 1*a*. As shown in the illustrated embodiment, fiber 601 connects to a collimator 602, which generates a beam 603. In the illustrated embodiment, beam 603 is configured with a wavelength bandwidth $\Delta\lambda$. In the illustrated embodiment, bandwidth $\Delta\lambda$ is configured to be split into three sub-bandwidths labeled: $\Delta\lambda_1$, $\Delta\lambda_2$, and $\Delta\lambda_3$. In one embodiment, the three sub-bandwidth wavelength contents do not overlap.

In the illustrated embodiment, beam 603 hits unit 604. In the illustrated embodiment, unit 604 is shown as a cube comprising faces having different coatings configured to realize beam splitting according to beam wavelength. For example, in the illustrated embodiment, face 605 of unit 604 reflects $\Delta\lambda_1$ and transmits $\Delta\lambda_2$ and $\Delta\lambda_3$. In the illustrated embodiment, face 610 reflects $\Delta\lambda_2$ and transmits $\Delta\lambda_1$ and $\Delta\lambda_3$. And in the illustrated embodiment, face 613 reflects $\Delta\lambda_3$ and transmits $\Delta\lambda_1$ and $\Delta\lambda_2$. One having ordinary skill in the art will understand that different methods can also be utilized to achieve a similar splitting.

In the illustrated embodiment, face 605 reflects $\Delta\lambda_1$ as beam 606 and transmits $\Delta\lambda_2$ and $\Delta\lambda_3$ as beam 609. As illustrated, beam 606 hits mirrors 607 and 608. In the illustrated embodiment, mirrors 607 and 608 are mirrors and are fixed on mount 618, which can move along direction 619. So configured, mount 618 can be employed to adjust the path-length of beam 606. Additionally, in the illustrated embodiment, mirror 608 is fixed on mount 620, which can move with respect to mount 618 along direction 621. As illustrated, after reflection on mirror 608, beam 606 transmits through face 610 and face 613 to location 614.

As described above, in the illustrated embodiment, the transmitted beam 609 comprises two sub-bandwidths $\Delta\lambda_2$ and $\Delta\lambda_3$. In the illustrated embodiment, sub-bandwidth $\Delta\lambda_2$ of beam 609 is reflected by face 610 to generate beam 611. Similarly, beam 609 is transmitted through face 610 to generate beam 612. As shown, beam 611 (having sub-bandwidth $\Delta\lambda_2$) is transmitted through face 613 to location 614.

In the illustrated embodiment, beam 612 hits mirrors 615 and 616. In the illustrated embodiment, mirrors 615 and 616 are fixed on a mount 622 that can move along direction 623. Similarly, mirror 616 is fixed on mount 624 that can move along direction 625 with respect to mount 622. One having ordinary skill in the art will appreciate that these movements can be configured to adjust the path length of beam 612.

After reflecting from mirror 616, beam 612 hits a plate 617 and is reflected by face 613 to location 614. In the illustrated embodiment, plate 617 is configured with a 45 degree angle with respect to the direction of propagation of beam 612. As such, one skilled in the art will understand that, in the illustrated embodiment, depending on its thickness, plate 617 therefore displaces beam 612 in the direction 626 as shown in view 650 of FIG. 6b.

In the illustrated embodiment, the three beams 606, 611, and 612, having respective sub-bandwidths $\Delta\lambda_1$, $\Delta\lambda_2$ and $\Delta\lambda_3$, exit MBGU 600 and are directed onto the scanning system, such as scanning unit 108 of FIG. 1a, for example. One having ordinary skill in the art will appreciate that these three beams are typically linearly independent and typically have parallel directions before hitting at three different locations of the scanning system (as shown in FIG. 3b, for example).

FIG. 6b shows a view 350 illustrating the three output beam locations in a plane perpendicular to their propagation direction at location 614 of FIG. 6a. In one embodiment, these locations can be changed by, for example, displacing mount 620 and mirror 608 to shift beam 606 with respect to beam 611 in the direction 621. Similarly, in one embodiment, by displacing mount 624 and mirror 616, beam 612 is shifted with respect to beam 611 in the direction 625. As described above, changing the thickness of plate 617 modifies the displacement along direction 625 of beam 612 with respect to beam 611. Accordingly, the illustrated embodiment, can be configured to help reduce the cross-talks between sub-bandwidths $\Delta\lambda_1$ and $\Delta\lambda_3$ interfering with the same reference light. Similarly, in one embodiment, sub-bandwidths $\Delta\lambda_2$ can be detected with a different (e.g., different reference path-length) reference light, cross-talks with other sub-bandwidths can be expected to be minimized.

Figure 7:
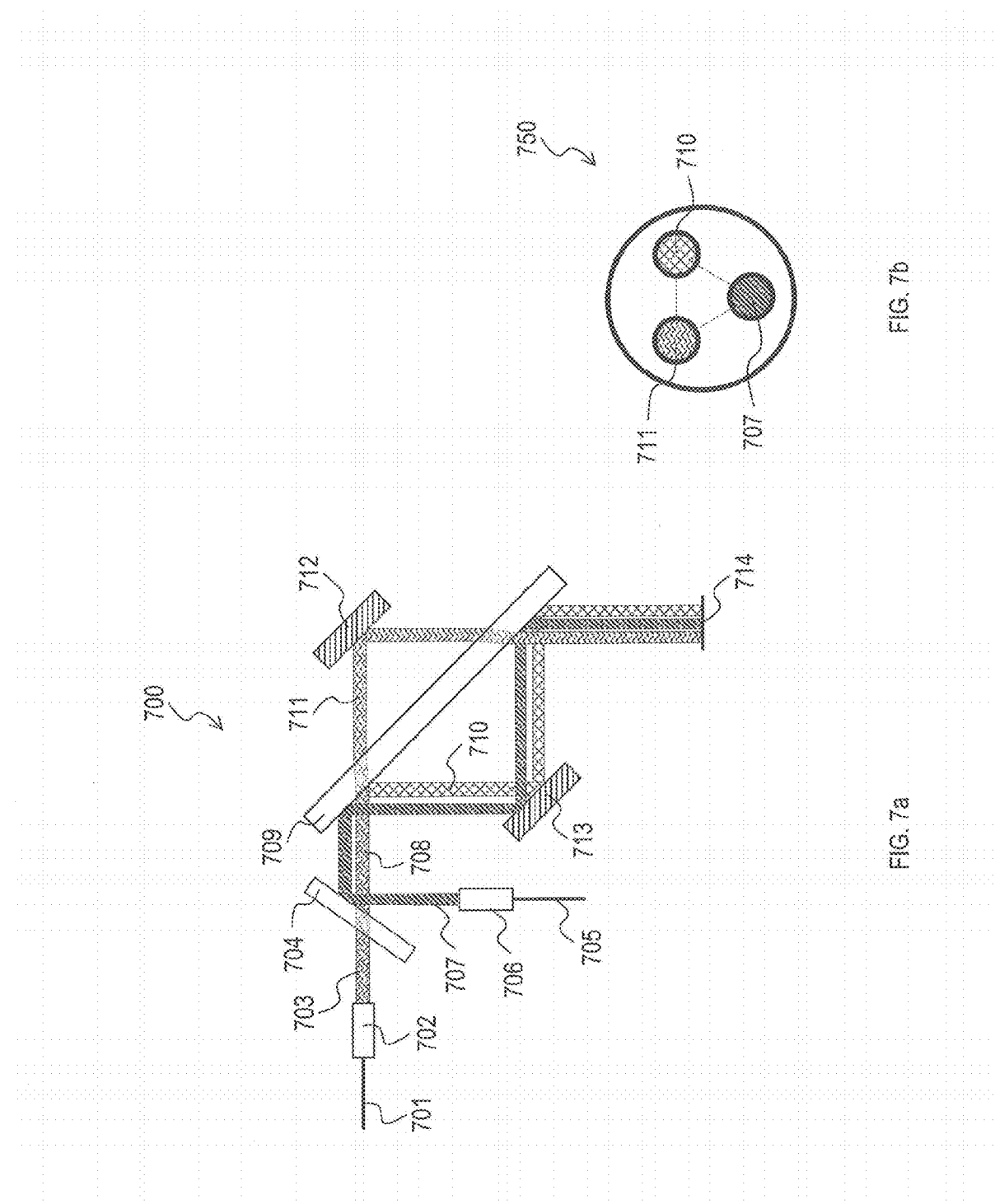
FIGS. 7a and 7b are block diagrams showing a multi-beam generator unit in accordance with still another embodiment.

FIGS. 7a and 7b are block diagrams showing an MBGU in yet another embodiment. The embodiments shown in FIGS. 7a and 7b can be configured to serve as, for example, MGBU 226 in FIG. 2. In the embodiment shown in FIG. 7a, MBGU 700 includes fiber 701. Fiber 701 corresponds to, for example, fiber 210 of FIG. 2 and fiber 705 corresponds to, for example, fiber 211 of FIG. 2. As shown in the illustrated embodiment, fiber 701 connects to a collimator 702, which generates a beam 703. Similarly, fiber 705 connects to a collimator 706, which generates a beam 707. In the illustrated embodiment, beams 703 and 707 are configured with a wavelength bandwidth $\Delta\lambda$. In the illustrated embodiment, bandwidth $\Delta\lambda$ is configured to be split into three sub-bandwidths labeled: $\Delta\lambda_1$, $\Delta\lambda_2$, and $\Delta\lambda_3$. In one embodiment, the three sub-bandwidth wavelength contents do not overlap.

In the illustrated embodiment, beam 703 hits unit 704. In the illustrated embodiment, unit 704 is configured to reflect wavelengths $\Delta\lambda_2$ and transmit wavelengths $\Delta\lambda_1$ and $\Delta\lambda_3$. As such, in the illustrated embodiment, the transmitted beam 708, towards unit 709, is composed of two sub-bandwidths $\Delta\lambda_1$ and $\Delta\lambda_3$. Similarly, only sub-bandwidth $\Delta\lambda_2$ of beam 707 is reflected by unit 704 towards unit 709. In the illustrated embodiment, beams 707 and 703 do not hit unit 704 at the same location and therefore, the transmitted and reflected beams generally do not spatially overlap and are not co-planar.

In the illustrated embodiment, unit 709 reflects sub-bandwidths $\Delta\lambda_1$ and $\Delta\lambda_2$ and transmits sub-bandwidth $\Delta\lambda_3$. Therefore, in the illustrated embodiment, beam 707 is reflected by unit 709 towards mirror 713. As shown, mirror 713 reflects beam 707 back to another location of unit 709. In the illustrated embodiment, unit 709 is shown as a single unit. In an alternate embodiment, unit 709 can be configured as two separate units with similar or different reflective properties. In the illustrated embodiment, unit 709 again reflects beam 707, to position 714.

In the illustrated embodiment, beam 708 is composed of sub-bandwidths $\Delta\lambda_1$ and $\Delta\lambda_3$. As such, when beam 708 hits unit 709, sub-bandwidth $\Delta\lambda_1$ is reflected as beam 710 towards mirror 713 and sub-bandwidth $\Delta\lambda_3$ is transmitted as beam 711 towards mirror 712. In the illustrated embodiment, after reflection on mirror 713, beam 710 is directed to unit 709, which reflects beam 710 to position 714. Similarly, in the illustrated embodiment, beam 711 is reflected by mirror 712 towards unit 709, which transmits beam 711 to position 714.

In the illustrated embodiment, the three beams 710, 707, and 711, having respective sub-bandwidths $\Delta\lambda_1$, $\Delta\lambda_2$ and $\Delta\lambda_3$, exit MBGU 700 (at position 714) and are directed onto the scanning system, such as scanning unit 227 of FIG. 2, for example. One having ordinary skill in the art will appreciate that these three beams are typically not co-planar and typically have parallel directions before hitting at three different locations of the scanning system (as shown in FIG. 3b, for example).

FIG. 7b shows a view 750 illustrating the three output beam locations in a plane perpendicular to their propagation direction at location 714 of FIG. 7a. In one embodiment, these locations can be changed by, for example, displacing collimator 706 to move beam 707 and mirror 712 to move beam 711. Accordingly, the illustrated embodiment can be configured to help reduce the cross-talks between overlapping sub-bandwidths. In one embodiment, adjusting the fiber lengths 701 and 705 allows reducing cross-talks between sub-bandwidths $\Delta\lambda_2$ and $\Delta\lambda_1$ and between sub-bandwidths $\Delta\lambda_2$ and $\Delta\lambda_3$.

Figure 8:
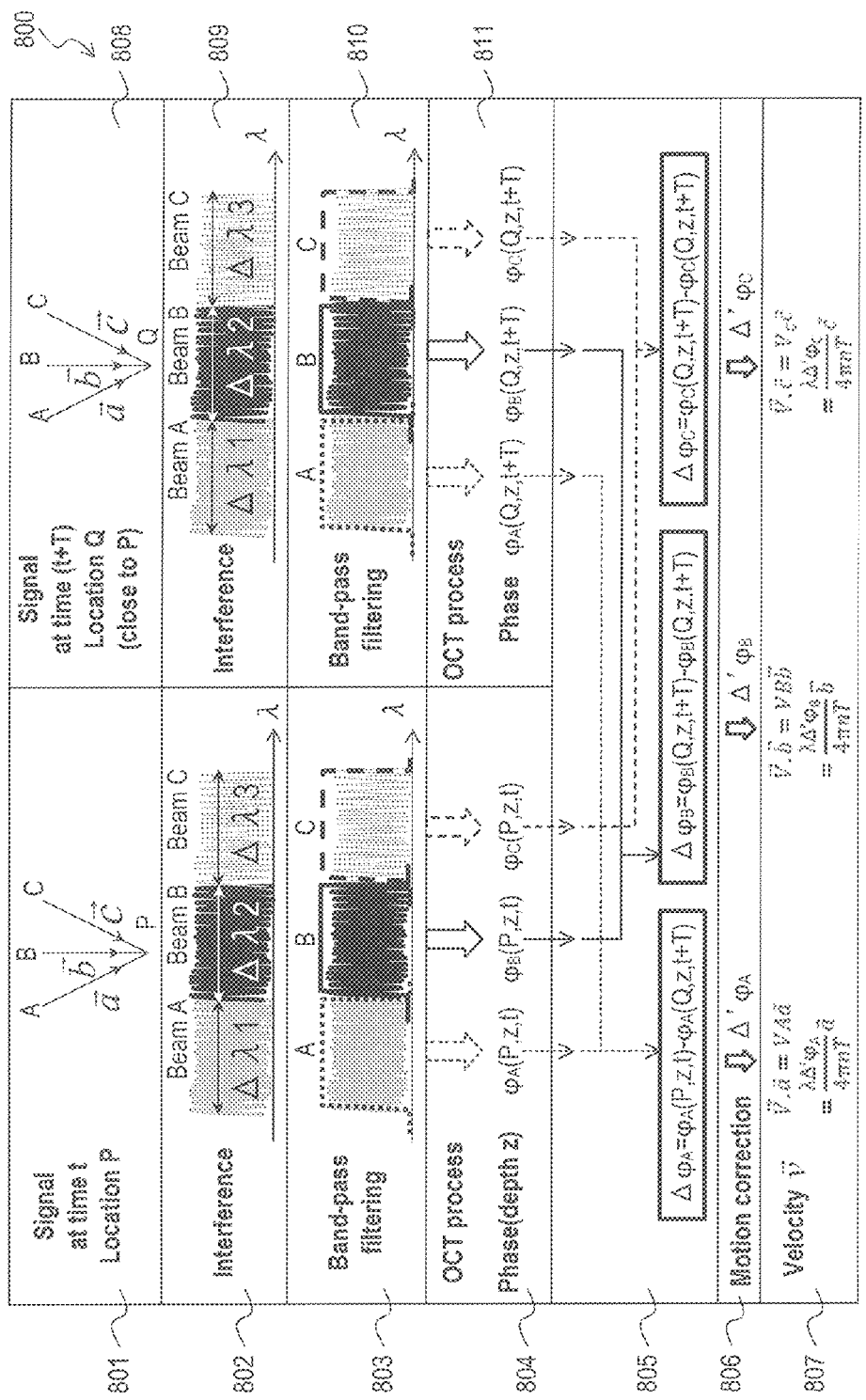
FIG. 8 is a block diagram showing a multi-channel optical coherence tomography method in accordance with one embodiment.

So configured, the embodiments described herein can be configured for OCT operations that overcome at least some of the disadvantages associated with legacy systems and methods. For example, FIG. 8 is a block diagram showing a process for obtaining absolute velocity of motions inside the sample from the signal acquired by, for example, the embodiments of FIGS. 1a/1b and 2. As described above, these embodiments allow scanning the sample transversally with three incident beams on the same location on the sample, having three different directions for each acquired position.

As shown in FIG. 8, two positions are considered: P (801) and Q (808). Incident scanning beams on the sample are denoted in FIG. 8 by A, B, and C. The directions of beams A, B, C are $\vec{a}$, $\vec{b}$, and $\vec{c}$ respectively. In the illustrated embodiment, these directions are linearly independent. Additionally, in the illustrated embodiment, it is assumed that measurements at positions P and Q onto the sample are acquired at time t and time t+T, respectively. Moreover, location Q is assumed near or "close to" P. One having ordinary skill in the art will understand that "Q close to P" means that the two locations are close enough to enable overlap between scanning beams, thereby allowing significant correlation between OCT signals.

In the illustrated embodiment, the acquired interference signal for positions P and Q is encoded in wavelengths (802 and 809). Wavelength bandwidths $\Delta\lambda_1$, $\Delta\lambda_2$, and $\Delta\lambda_3$ correspond to beams A, B, and C respectively. In the illustrated embodiment, a first step is to apply band-pass filters on the interference signal such as to isolate the three bands corresponding to each beam (803 and 810). One having ordinary skill in the art will appreciate that different shape of band-pass filtered can be applied to perform this filtering. Then, for each band-pass filtered signal, the optical coherence tomography (OCT) process is applied to obtain a complex OCT signal composed of an amplitude and a phase information as a function of the depth z (804 and 811). Therefore, phases $\phi_A(P,z,t)$, $\phi_B(P,z,t)$, and $\phi_C(P,z,t)$ are obtained for beams A, B and C, respectively. Therefore, at location Q, phases $\phi_A(Q,z,t+T)$, $\phi_B(Q,z,t+T)$, and $\phi_C(Q,z,t+T)$ are obtained for beams A, B, and C, respectively. For each beam the following phase differences are calculated (805):

$$\Delta\phi_A = \phi_A(P,z,t) - \phi_A(Q,z,t+T), \Delta\phi_B = \phi_B(P,z,t) - \phi_B(Q,z,t+T), \text{ and } \Delta\phi_C = \phi_C(Q,z,t+T) - \phi_C(Q,z,t+T).$$

After correction of sample motion artifacts (806), previous phase differences $\Delta\phi_A$, $\Delta\phi_B$, and $\Delta\phi_C$ are changed to $\Delta'\phi A$, $\Delta'\phi B$, and $\Delta'\phi C$. Then, velocity $V_A$, $V_B$, and $V_C$ along beam direction $\vec{a}$, $\vec{b}$, and $\vec{c}$, respectively, can be computed as:

$$V\vec{Aa} = \frac{\lambda\Delta'\phi A}{4\pi nT}\vec{a}, V\vec{Bb} = \frac{\lambda\Delta'\phi B}{4\pi nT}\vec{b} \text{ and } V\vec{Cc} = \frac{\lambda\Delta'\phi C}{4\pi nT}\vec{c},$$

with $\lambda$ being the central wavelength of the light source, n being the sample refractive index (807). Assuming that directions $\vec{a}$, $\vec{b}$, and $\vec{c}$ are known in a given reference frame, the velocity of motions inside the sample can be retrieved.

Figure 9:
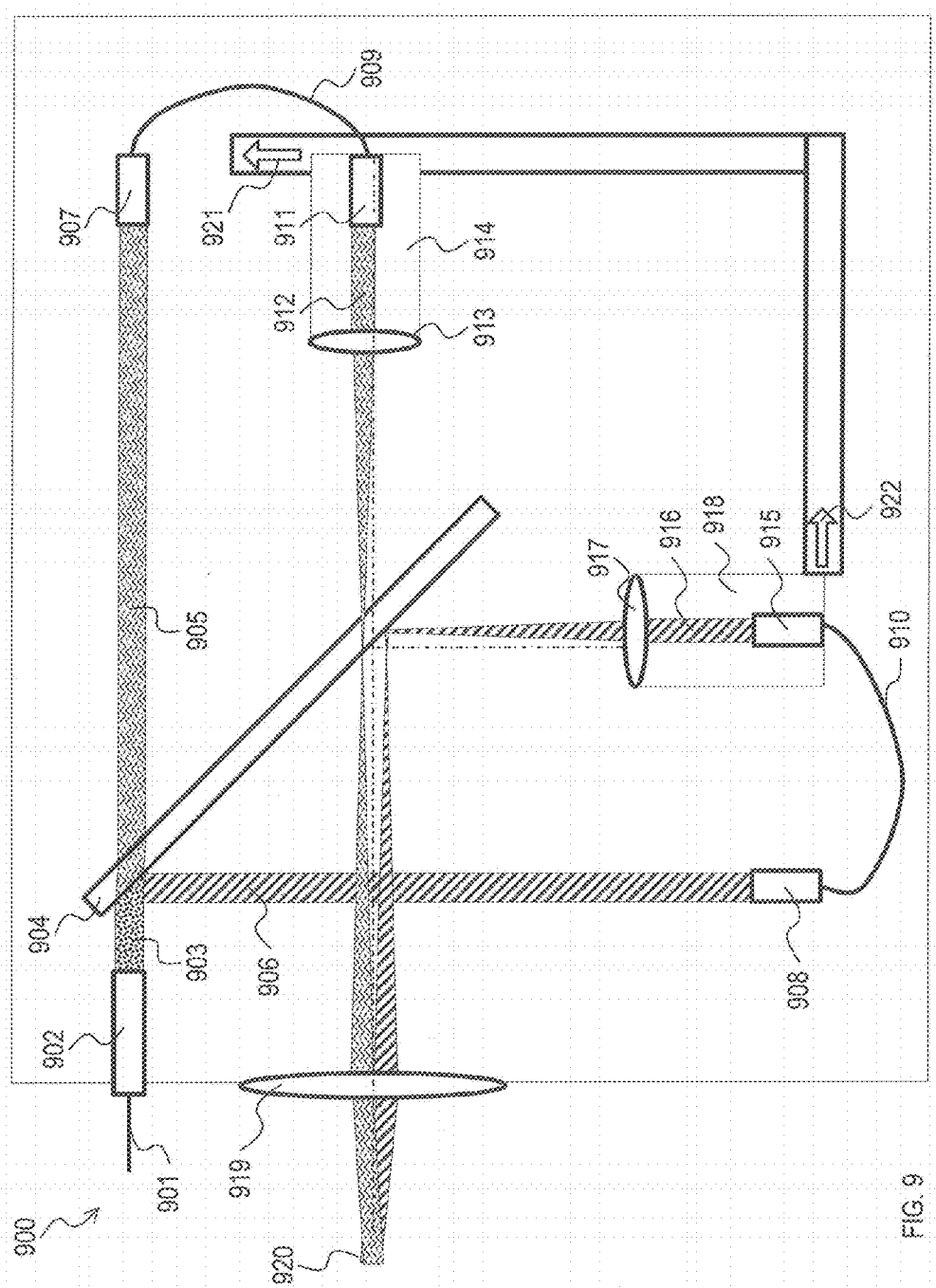
FIG. 9 is a block diagram showing a multi-beam generator unit in accordance with another embodiment.

As described above, the disclosed embodiments can be configured for a variety of OCT techniques. For example, FIG. 9 is a block diagram showing an MBGU 900 in another embodiment, which can be configured such as MBGU 107 of FIG. 1a, for example. In the illustrated embodiment, MBGU 900 can be configured to provide two beams whose incident angle is the same for a given location on the sample and that scan the sample with a variable delay between each other, allowing imaging, via OCT, of motions inside the sample with different velocities.

In the illustrated embodiment, fiber 901 can be configured to correspond to fiber 104 of FIG. 1. In the illustrated embodiment, fiber 901 directs light having wavelength bandwidth $\Delta\lambda$ to collimator 902. As shown in the illustrated embodiment, collimator 902 generates a beam 903 that is directed to a dichroic mirror 904. In the illustrated embodiment, dichroic mirror 904 splits beam 903 into two bandwidths: $\Delta\lambda_1$ is transmitted and forms beam 905, and $\Delta\lambda_2$ is reflected and forms beam 906.

Beam 905 is collected by collimator 907, which passes beam 905 via fiber 909 to collimator 911, exiting as beam 912. In the illustrated embodiment, beam 912 exits collimator 911, hits the lens 913, is transmitted through dichroic mirror 904, and reaches lens 919. In the illustrated embodiment, collimator 911 and lens 913 are attached to a moving plate 914 that allows moving the beam 912 back and forth as desired along direction 921.

In the illustrated embodiment, beam 906 is collected by collimator 908, which passes beam 906 through fiber 910 to collimator 915, exiting as beam 916. In the illustrated embodiment, beam 916 exits collimator 915, hits the lens 917, is reflected by the dichroic mirror 904, and reaches lens 919. In the illustrated embodiment, collimator 915 and lens 917 are attached to a moving plate 918 that allows moving the beam 916 back and forth along direction 922.

In the illustrated embodiment, after passing through lens 919, beams 912 and 916 intersect at the focal point 920 of lens 919. In one embodiment, focal point 920 corresponds to the pivot point of a scanning system, such as scanning system 108 of FIG. 1a, for example. However, one having ordinary skill in the art will appreciate that off-pivot positioning can be used, for example, for full-range imaging. Similarly, displacing plates 914 and 918 along directions 921 and 922 respectively allows changing the intersecting angle of beams 912 and 916 on the scanning system.

Figure 10:
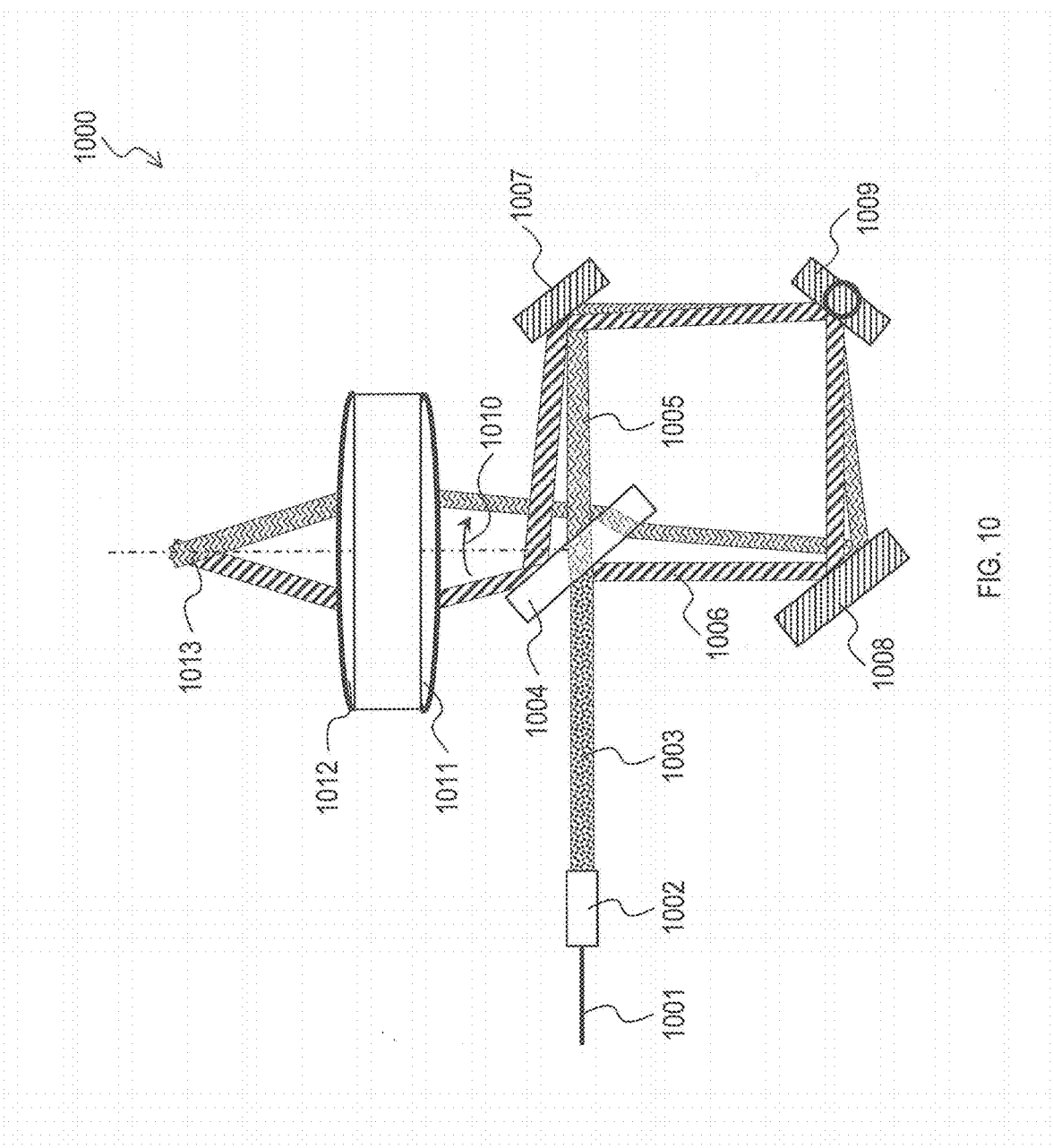
FIG. 10 is a block diagram showing a multi-beam generator unit in accordance with another embodiment.

FIG. 10 is a block diagram showing an MBGU 1000 in another embodiment, which can be configured such as MBGU 107 of FIG. 1a, for example. In the illustrated embodiment, MBGU 1000 can be configured to provide two beams that scan the sample with a variable delay between the beams, allowing imagining, via OCT methods, of motions inside the sample with different velocities.

In the illustrated embodiment, fiber 1001 can be configured to correspond to fiber 104 of FIG. 1a. In the illustrated embodiment, fiber 1001 directs light having wavelength bandwidth $\Delta\lambda$ to collimator 1002. As shown in the illustrated embodiment, collimator 1002 generates a beam 1003 that is directed to a dichroic mirror 1004. In the illustrated embodiment, dichroic mirror 1004 splits beam 1003 into two bandwidths: $\Delta\lambda_1$ is transmitted and forms beam 1005, and $\Delta\lambda_2$ is reflected and forms beam 1006.

In the illustrated embodiment, beam 1005 is reflected by mirror 1007 to mirror 1009. In the illustrated embodiment, mirror 1009 is configured to be rotated so as to change the direction of reflected light. In the illustrated embodiment, mirror 1009 reflects beam 1005 to mirror 1008. As shown, mirror 1008 redirects beam 1005 to dichroic mirror 1004. In the illustrated embodiment, dichroic mirror 1004 transmits beam 1005 to lens 1011.

In the illustrated embodiment, beam 1006 is reflected from dichroic mirror 1004 to mirror 1008. Similarly, mirror 1008 reflects beam 1006 to mirror 1009. As shown, mirror 1009 redirects beam 1006 to mirror 1007. And mirror 1007 reflects beam 1006 to dichroic mirror 1004, which reflects beam 1006 to lens 1011.

Before entering lens 1011 in the forward direction, an angle 1010 describes the angle between the directions of beams 1005 and 1006. In the illustrated embodiment, the mirror 1009 pivot point is positioned at the focal point of lens 1011 such that when mirror 1009 is rotated, the directions of beams 1005 and 1006 after lens 1012 intersect at the lens 1012 focal position 1013. In one embodiment, focal position 1013 corresponds to the pivot point of a scanning system, such as scanning system 108 of FIG. 1a, for example. However, one having ordinary skill in the art will appreciate that off-pivot positioning can be used, for example, for full-range imaging. Additionally, in the illustrated embodiment, rotating the mirror 1009 allows changing the intersecting angle of beams 1005 and 1006 on the scanning system. Consequently, in one embodiment, changing this intersecting angle alters the distance between beams on the sample.

Figure 11:
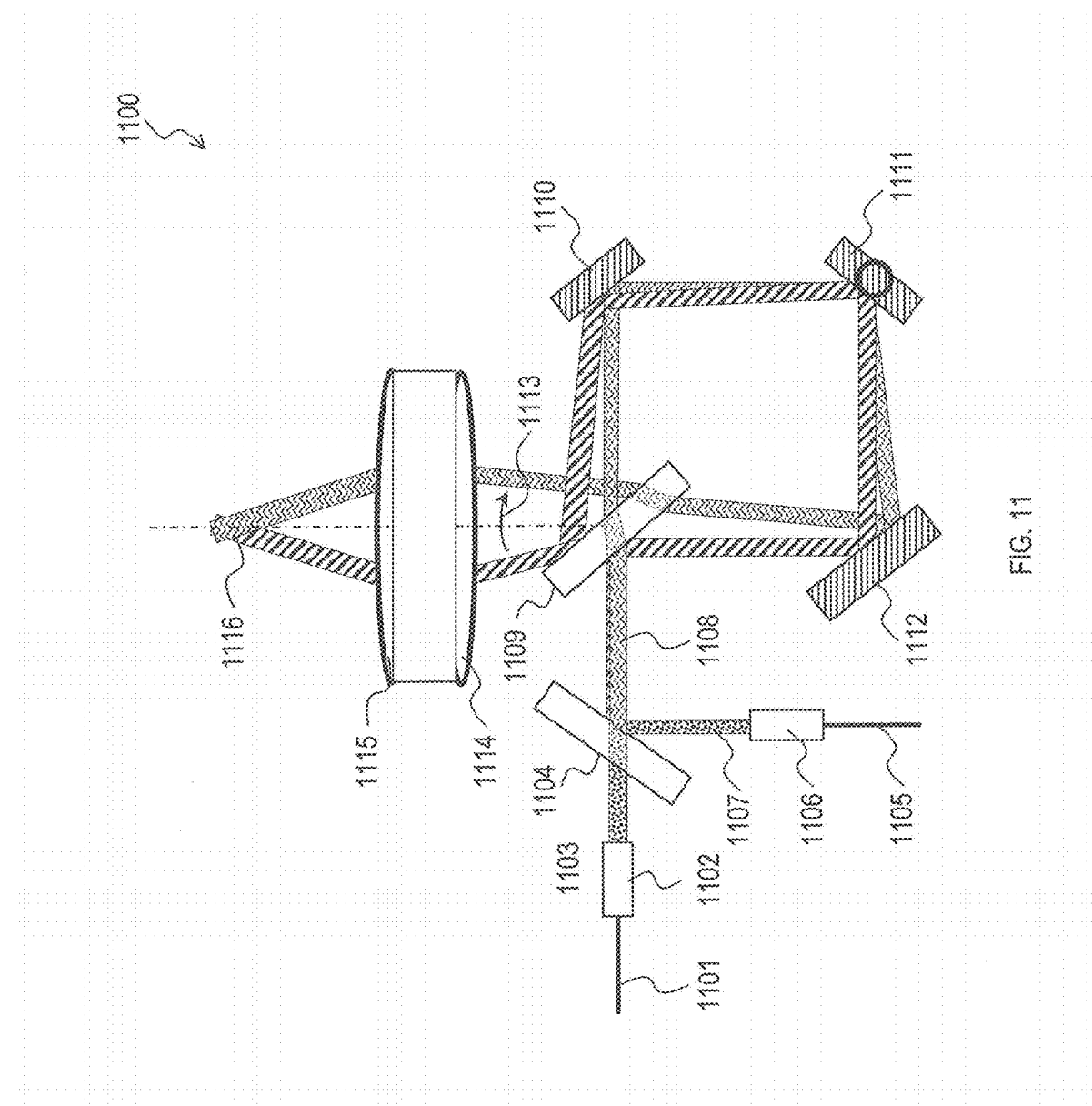
FIG. 11 is a block diagram showing a multi-beam generator unit in accordance with another embodiment.

FIG. 11 is a block diagram showing an MBGU 1100 in another embodiment, which can be configured such as MBGU 226 of FIG. 2, for example. In the illustrated embodiment, MBGU 1100 can be configured to provide two beams that scan the sample with a variable delay between the beams, allowing imagining, via OCT methods, of motions inside the sample with different velocities.

In the illustrated embodiment, the EMR source is configured to provide light having a wavelength bandwidth $\Delta\lambda$ that can be split into two sub-bandwidths labeled: $\Delta\lambda_1$ and $\Delta\lambda_2$. In the illustrated embodiment, fiber 1101 can be configured to correspond to fiber 210 of FIG. 2. In the illustrated embodiment, fiber 1105 can be configured to correspond to fiber 211 of FIG. 2.

In the illustrated embodiment, collimator 1102 (1106) emits a beam 1103 (1107) that is directed to a dichroic mirror 1104. In the illustrated embodiment, dichroic mirror 1104 transmits wavelength bandwidth $\Delta\lambda_1$ and reflects wavelength bandwidth $\Delta\lambda_2$. Accordingly, as shown, dichroic mirror 1104 transmits bandwidth $\Delta\lambda_1$ of beam 1103, labeled as beam 1108. Dichroic mirror 1104 reflects bandwidth $\Delta\lambda_2$ of beam 1107. Both beams 1108 and 1107 hit dichroic mirror 1109.

In the illustrated embodiment, dichroic mirror 1109 is configured, for example, with similar reflective properties as dichroic mirror 1104, therefore beam 1108 is transmitted through dichroic mirror 1109 and is directed to mirror 1110. As shown, beam 1107 is reflected by dichroic mirror 1109 towards mirror 1112.

In the illustrated embodiment, beam 1108 is consecutively reflected by mirrors 1110, 1111, and 1112 to reach dichroic mirror 1109, where it is transmitted to lenses 1114 and 1115. Similarly, beam 1107 is consecutively reflected by mirrors 1112, 1111, and 1110 to reach dichroic mirror 1109, where it is reflected to lenses 1114 and 1115.

Before entering lens 1114 in the forward direction, an angle 1113 describes the angle between directions of beams 1107 and 1108. In the illustrated embodiment, the mirror 1111 pivot point is positioned at the focal point of lens 1114 such as when mirror 1111 is rotated, the direction of beams 1107 and 1108 intersect at the lens 1115 focal position 1116. In one embodiment, focal position 1116 corresponds to the pivot point of a scanning system, such as scanning system 227 of FIG. 2, for example. However, one having ordinary skill in the art will appreciate that off-pivot positioning can be used, for example, for full-range imaging.

In the illustrated embodiment, rotating the mirror 1111 allows changing the intersecting angle of beams 1107 and 1108 on the scanning system. As such, in the illustrated embodiment, changing this intersecting angle alters the distance between beams on the sample. In comparison with the embodiment described with respect to FIG. 10, the embodiment described with respect to FIG. 11 allows reduction of the cross-talks by adjusting lengths of fiber 1101 and 1105, such that their half-difference is longer than the coherence length of the light source.

Figure 12:
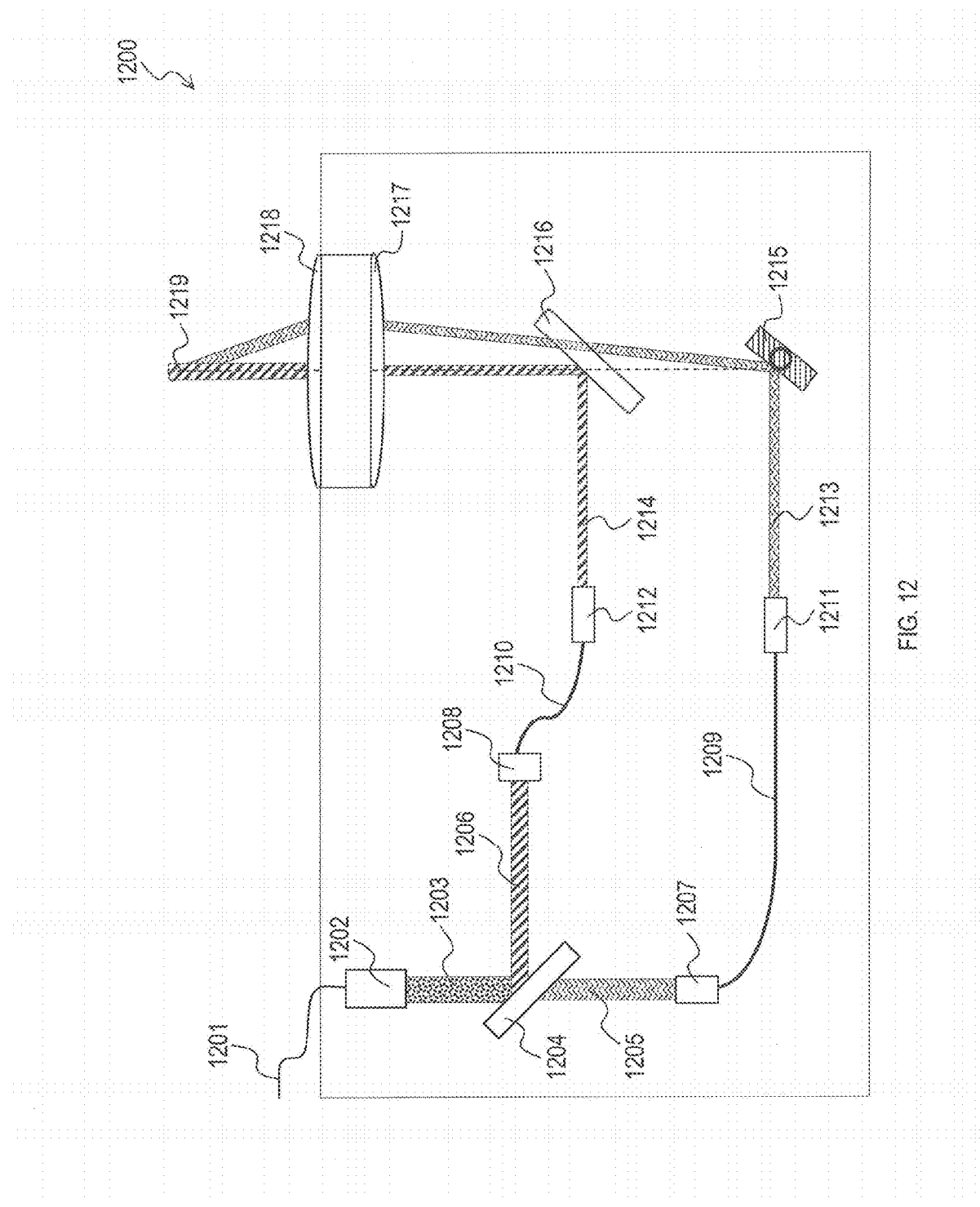
FIG. 12 is a block diagram showing a multi-beam generator unit in accordance with another embodiment.

FIG. 12 is a block diagram showing an MBGU 1200 in yet another embodiment, which can be configured such as MBGU 107 of FIG. 1a, for example. In the illustrated embodiment, MBGU 1200 can be configured to provide two beams that scan the sample with a variable delay between each other, allowing imaging, via OCT, of motions inside the sample with different velocities.

In the illustrated embodiment, fiber 1201 can be configured to correspond to fiber 104 of FIG. 1. In the illustrated embodiment, fiber 1201 directs light having wavelength bandwidth $\Delta\lambda$ to collimator 1202. As shown in the illustrated embodiment, collimator 1202 generates a beam 1203 that is directed to a dichroic mirror 1204. In the illustrated embodiment, dichroic mirror 1204 splits beam 1203 into two bandwidths: $\Delta\lambda_1$ is transmitted and forms beam 1205, and $\Delta\lambda_2$ is reflected and forms beam 1206.

In the illustrated embodiment, beam 1205 is collected by collimator 1207, which passes beam 1205 via fiber 1209 to collimator 1211, exiting as beam 1213. In the illustrated embodiment, beam 1213 exits collimator 1211 and hits mirror 1215. In the illustrated embodiment, mirror 1215 reflects beam 1213 to dichroic mirror 1216. In the illustrated embodiment, beam 1213 is transmitted through dichroic mirror 1216 and reaches lens 1217. As shown, lens 1217 deflects beam 1213 to lens 1218. Similarly, lens 1218 redirects beam 1213 to its image focal point 1219.

In the illustrated embodiment, beam 1206 is collected by collimator 1208, which passes beam 1206 via 1210 to collimator 1212. One having ordinary skill in the art will understand that, in one embodiment, collimators 1211 and 1212 and fibers 1209 and 1210 can be replaced by bulk optics. One having ordinary skill in the art will understand that, in an alternate embodiment, components from collimator 1202 to collimators 1212 and 1211 could be replaced by a simple fiber coupler or a wavelength division multiplexer. Additionally, in an alternate embodiment, a single dichroic mirror can be used instead of two.

In the illustrated embodiment, beam 1214 exits collimator 1212 and hits dichroic mirror 1216. As shown, beam 1214 is reflected by dichroic mirror 1216 and is directed to lens 1217. Similarly, beam 1214 is transmitted through lens 1218 and reaches image focal point 1219 of lens 1218. In the illustrated embodiment, the mirror 1215 pivot point corresponds to the object focal point of lens 1217. In one embodiment, the mirror 1215 pivot point is the conjugate of point 1219. As such, in one embodiment, when mirror 1215 is rotated, the angle between beams at point 1219 is changed with conservation of the intersecting point. In one embodiment, the focal point 1219 corresponds to the pivot point of a scanning system, such as scanning system 1408 of FIG. 1a, for example. Accordingly, one having ordinary skill in the art will understand that, in one embodiment, changing this intersecting angle alters the distance between beams on the sample.

Figure 13:
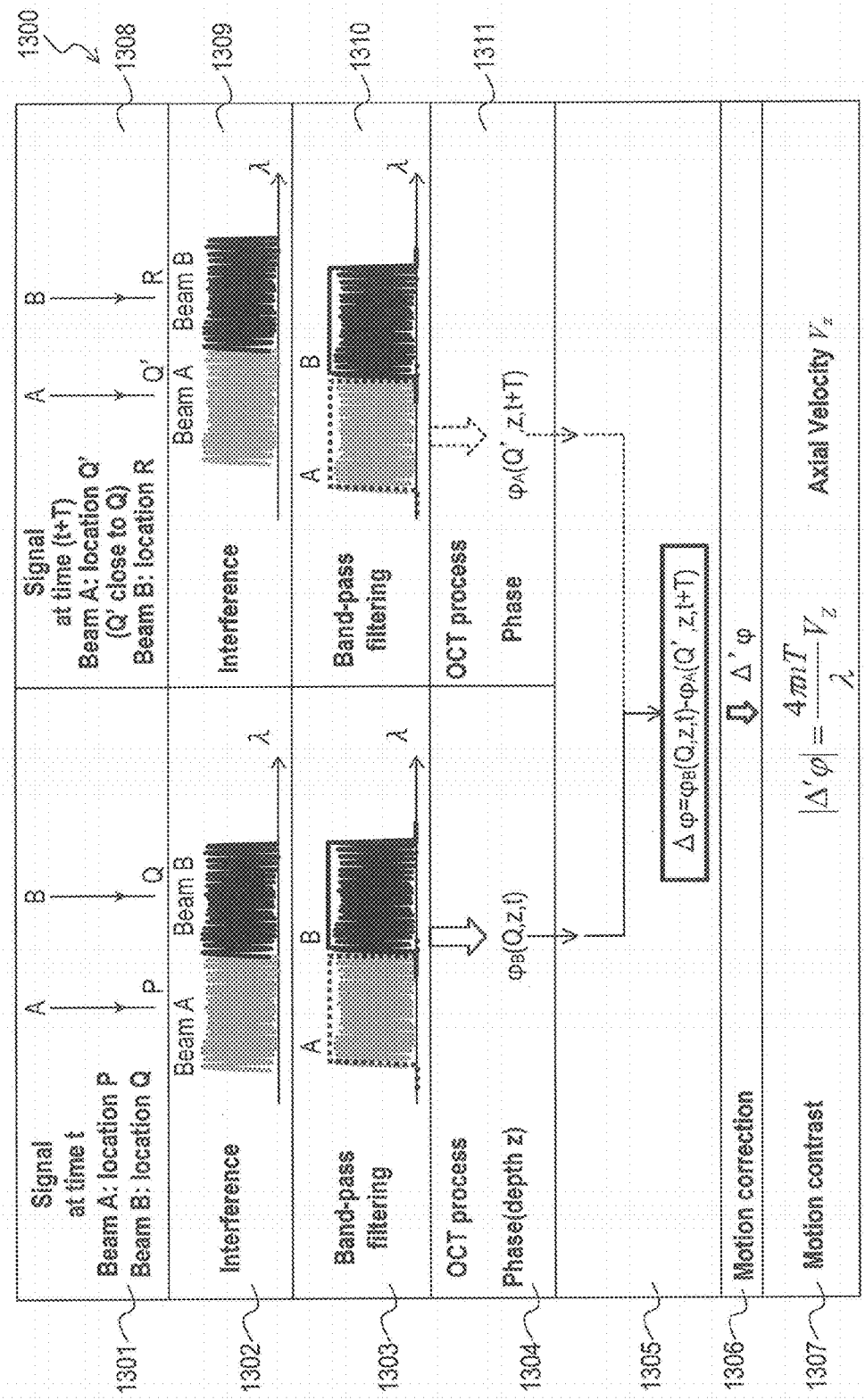
FIG. 13 is a block diagram showing a multi-channel optical coherence tomography method in accordance with one embodiment.

So configured, the embodiments described herein can be configured for OCT operations that overcome at least some of the disadvantages associated with legacy systems and methods. For example, FIG. 13 is a block diagram showing a process for obtaining absolute velocity of motions inside the sample from the signal acquired by, for example, the embodiments of FIGS. 1a/1b and 2. As described above, these embodiments allow scanning the sample transversally with two incident beams at two different locations on the sample. As such, by scanning the sample, an overlap exists between locations of these two beams allowing improved motion contrast imaging.

As shown in FIG. 13 (1301), the two beams are denoted by A and B. At instant t (1301) a measurement is carried where beams A and B are at positions P and Q respectively. At instant t+T (1308), a measurement is carried out where beams A and B are positions Q' and R. In the illustrated embodiment, it is assumed that positions Q and Q' onto the sample are "near" or "close to" each other. One having ordinary skill in the art will understand that "close" means that the two locations are close enough to enable overlap between scanning beams allowing significant correlation between OCT signals.

In the illustrated embodiment, the acquired interference signal at time t for positions P (beam A) and Q (beam B) is encoded in wavelength (1302) where beam A and beam B correspond to wavelength bandwidths $\Delta\lambda_1$ and $\Delta\lambda_2$, respectively. Similarly, the acquired interference signal at time t+T for positions Q' (beam A) and R (beam B) is encoded in wavelength (1309), where beam A and beam B correspond to wavelength bandwidths $\Delta\lambda_1$ and $\Delta\lambda_2$, respectively.

In the illustrated embodiment, a first step is to apply band-pass filters on the interference signal such as to isolate the two bands corresponding to each beam (1303 and 1310). One having ordinary skill in the art will understand that different shapes of band-pass filters can be applied to perform this filtering. Then, for each band-pass filtered signal, the optical coherence tomography (OCT) process is applied to obtain a complex OCT signal composed of an amplitude and a phase information as a function of the depth z (1304 and 1311).

In the illustrated embodiment, because positions Q and Q' are close, their OCT signals are correlated and comparison is possible. In the following OCT phases are compared but one having ordinary skill in the art will understand that different methods using the intensity information are feasible such as, for example, amplitude decorrelation of speckle decorrelation methods. In the illustrated embodiment, for position Q, the phase of beam B acquired at time t is $\phi_B(Q,z,t)$ (where z corresponds to the depth) and for position Q', the phase of beam A acquired at time t+T is: $\phi_A(Q',z,t+T)$. In one embodiment, a phase difference is computed (1305) as:

$$\Delta\phi = \phi_B(Q,z,t) - \phi_A(Q',z,t+T).$$

After correcting the phase difference for motions artifacts $\Delta\phi$ is written $\Delta'\phi$ (1306). Finally, computing, for example, the absolute value $|\Delta'\phi|$ or the square $\Delta'\phi^2$, motion contrast imaging is obtained. Additionally, one having ordinary skill in the art will understand from (1307) that $$|\Delta'\phi| = \frac{4\pi nT}{\lambda} V_z$$

where n is the refractive index of sample, $\lambda$ is the central wavelength of the light source and $V_z$ is the axial velocity of motions inside the sample. In the illustrated embodiment, if the velocity $V_z$ is small, a large delay T is needed to increase $|\Delta'\phi|$ above the measurement noise.

One skilled in the art will appreciate that variations of the above-disclosed and other features and functions, or alternatives thereof, may be desirably combined into many other different systems or applications. Additionally, various presently unforeseen or unanticipated alternatives, modifications, variations or improvements therein may be subsequently made by those having ordinary skill in the art, which are also intended to be encompassed by the following claims.

What is claimed is:

1. An optical coherence tomography apparatus, comprising:
   a first electro-magnetic radiation (EMR) source configured to provide EMR to a first optical path and a second optical path, wherein the first optical path is associated with a sample and the second optical path is associated with a reference;
   a multi-beam generator unit (MBGU) coupled to the first optical path and a scanning system, the MBGU being configured to generate a first EMR beam and a second EMR beam, the first EMR beam having different wavelength contents than the second EMR beam;
   the MBGU being further configured to provide the first EMR beam and the second EMR beam to the scanning system;
   the scanning system being configured to illuminate the sample at a first location and a second location of the sample, the second location being near to the first location, at a first time and a second time, with both the first EMR beam and the second EMR beam;
   an interference module coupled to the first optical path and the second optical path, the interference module being configured to generate interference signals based on received EMR returning from the reference and the first EMR beam and the second EMR beam returning from the sample;
   a detector coupled to the interference module, the detector being configured to generate detection signals based on received interference signals; and
   a processor coupled to the detector, the processor being configured to process detection signals received from the detector and to generate optical coherence tomography data based on the processed detection signals.

2. The apparatus according to claim 1, wherein the MBGU is further configured to generate the first EMR beam and the second EMR beam to comprise variable relative directions.

3. The apparatus according to claim 1, wherein the scanning system comprises a pivot point and the MBGU is further configured to provide the first EMR beam and the second EMR beam so as to intersect with the pivot point.

4. The apparatus according to claim 2, wherein generating the first EMR beam and the second EMR beam to comprise variable relative directions comprises manipulating optical components including at least one of the following: selecting or moving one of the plurality of optical paths wherein each optical paths comprises a dedicated optical fiber; a fiber Bragg grating, a blazed grating; a dispersive medium; an optical switch; a dichroic mirror; a wavelength division multiplexer; and moving a mirror to change relative directions or distances between the first EMR beam and the second EMR beam.

5. The apparatus according to claim 1, wherein the MBGU is further configured to generate the first EMR beam and the second EMR beam to comprise overlapping wavelength contents.

6. The apparatus according to claim 1, wherein the MBGU is further configured to generate the first EMR beam and the second EMR beam without regard to a polarization relationship between the first EMR beam and the second EMR beam.

7. The apparatus according to claim 1, wherein the optical coherence tomography data comprises at least one of the following: a phase difference; an absolute phase difference; a square of the phase difference; a phase variance; an amplitude decorrelation and a speckle decorrelation between at least two complex OCT signals originating from the first and the second locations.

8. The apparatus according to claim 1, wherein the processor is further configured to reduce motion artifacts.

9. The apparatus according to claim 1, wherein the first optical path and the second optical path share common optical components.

10. The apparatus according to claim 1, wherein the processor is further configured to compare at least two complex OCT signals originating from the first and the second locations.

11. An optical coherence tomography method, comprising:
provide electro-magnetic radiation (EMR) to a first optical path and a second optical path, wherein the first optical path is associated with a sample and the second optical path is associated with a reference;
generating a first EMR beam and a second EMR beam, the first EMR beam having different wavelength contents than the second EMR beam;
providing the first EMR beam and the second EMR beam to a scanning system;
illuminating the sample at a first location and a second location of the sample, the second location being near to the first location, at a first time and a second time, with both the first EMR beam and the second EMR beam;
generating interference signals based on received EMR returning from the reference and the first EMR beam and the second EMR beam returning from the sample;
generating detection signals based on the interference signals; and
processing detection signals to generate optical coherence tomography data based on the processed detection signals.

12. An optical coherence tomography apparatus, comprising:
a first electro-magnetic radiation (EMR) source configured to provide EMR to a first optical path and a second optical path, wherein the first optical path is associated with a sample and the second optical path is associated with a reference;
a multi-beam generator unit (MBGU) coupled to the first optical path and a scanning system, the MBGU being configured to generate a first EMR beam, a second EMR beam, and a third EMR beam, the first EMR beam, the second EMR beam, and the third EMR beam having different wavelength contents;
the MBGU being further configured to provide the first EMR beam, the second EMR beam, and the third EMR beam to the scanning system;
the scanning system being configured to illuminate the sample at a first point with the first EMR beam, the second EMR beam, and the third EMR beam such that, at the sample surface, the first EMR beam, the second EMR beam, and the third EMR beam comprise linearly independent vectors;
an interference module coupled to the first optical path and the second optical path, the interference module being configured to generate interference signals based on received EMR returning from the reference and the first EMR beam, the second EMR beam, and the third EMR beam returning from the sample;
a detector coupled to the interference module, the detector being configured to generate detection signals based on received interference signals; and
a processor coupled to the detector, the processor being configured to process detection signals received from the detector and to generate optical coherence tomography data based on the processed detection signals.

13. The apparatus according to claim 12, wherein the MBGU is further configured to generate the first EMR beam, the second EMR beam, and the third EMR beam to comprise variable relative distances.

14. The apparatus according to claim 12, wherein the MBGU is further configured to generate the first EMR beam, the second EMR beam, and the third EMR beam by manipulating optical components including at least one of the following: one of a plurality of optical paths wherein each optical path comprises a dedicated optical fiber; a fiber Bragg grating, a blazed grating; a dispersive medium; an optical switch; a dichroic mirror; a wavelength division multiplexer; and a mirror.

15. The apparatus according to claim 12, wherein the MBGU is further configured to generate the first EMR beam, the second EMR beam, and the third EMR beam to comprise overlapping wavelength contents.

16. The apparatus according to claim 12, wherein the MBGU is further configured to generate the first EMR beam, the second EMR beam, and the third EMR beam without regard to a polarization relationship between the first EMR beam, the second EMR beam, and the third EMR beam.

17. The apparatus according to claim 12, wherein the processor is further configured to calculate at least three phase differences of at least six complex OCT signals originating from at least one nearby position on the sample.

18. The apparatus according to claim 12, wherein the processor is further configured to reduce motion artifacts.

19. The apparatus according to claim 12, wherein the first optical path and the second optical path share common optical components.

20. An optical coherence tomography method, comprising:
providing electro-magnetic radiation (EMR) to a first optical path and a second optical path, wherein the first optical path is associated with a sample and the second optical path is associated with a reference;
generating a first EMR beam, a second EMR beam, and a third EMR beam, the first EMR beam, the second EMR beam, and the third EMR beam having different wavelength contents;
providing the first EMR beam, the second EMR beam, and the third EMR beam to a scanning system;
illuminating the sample at a first point with the first EMR beam, the second EMR beam, and the third EMR beam such that the first EMR beam, the second EMR beam, and the third EMR beam comprise linearly independent vectors;
generating interference signals based on received EMR returning from the reference and the first EMR beam, the second EMR beam, and the third EMR beam returning from the sample;
generating detection signals based on received interference signals; and
processing detection signals received from the detector and to generate optical coherence tomography data based on the processed detection signals.

* * * * *